(12) United States Patent
Montrose

(10) Patent No.: US 11,135,412 B2
(45) Date of Patent: Oct. 5, 2021

(54) SKIN THERAPY SYSTEMS

(71) Applicant: ParaffinUSA, LLC, Phoenix, AZ (US)

(72) Inventor: Deanna Montrose, Phoenix, AZ (US)

(73) Assignee: PARAFFINUSA, LLC, Phoenix, AZ (US)

( * ) Notice: Subject to any disclaimer, the term of this patent is extended or adjusted under 35 U.S.C. 154(b) by 0 days.

(21) Appl. No.: 16/840,426

(22) Filed: Apr. 5, 2020

(65) Prior Publication Data

US 2020/0230386 A1    Jul. 23, 2020

Related U.S. Application Data

(63) Continuation-in-part of application No. 15/979,459, filed on May 14, 2018, now abandoned.
(Continued)

(51) Int. Cl.

| | |
|---|---|
| *A61M 35/00* | (2006.01) |
| *A61K 8/02* | (2006.01) |
| *A61K 8/31* | (2006.01) |
| *A61K 8/92* | (2006.01) |
| *A61Q 19/00* | (2006.01) |

(52) U.S. Cl.
CPC ........... *A61M 35/10* (2019.05); *A61K 8/0204* (2013.01); *A61K 8/31* (2013.01); *A61K 8/922* (2013.01); *A61Q 19/00* (2013.01); *A61K 2800/87* (2013.01); *A61M 2205/3368* (2013.01); *A61M 2205/3686* (2013.01); *A61M 2205/59* (2013.01); *A61M 2210/083* (2013.01); *A61M 2210/086* (2013.01)

(58) Field of Classification Search
CPC . A61K 8/31; A61K 8/922; A61K 8/92; A61K 8/0204; A61K 2800/87; A61Q 19/00; A61M 35/003; A61M 35/00; A61M 35/10; A61M 2210/083; A61M 2210/086; A61M 2205/3368; A61M 2205/59; A61M 2205/3686; A45D 26/0014
See application file for complete search history.

(56) References Cited

U.S. PATENT DOCUMENTS 2,210,618 A * 8/1940 De St. Cyr ........... A61M 35/10
                                                                    604/292
4,122,554 A * 10/1978 Stager ................ A41D 19/0068
                                                                    2/164

(Continued)

*Primary Examiner* — Peter C English
(74) *Attorney, Agent, or Firm* — Katten Muchin Rosenman LLP

(57) ABSTRACT

The disclosed invention provides a skin therapy system for skin conditioning or treatment of a body part. The skin therapy system includes a body part shaped encaser including a first and second film substrate and an encaser liner disposed between the first and second film substrates. An outer peripheral edge of the encaser liner is sealed between outer peripheral edges of the first and second film substrates to create a hermetic seal forming a first fillable space between the first film substrate and a first layer of the encaser liner, a second fillable space between the second film substrate and a second layer of the encaser liner, and an internal volume defined by the first and second layers of the encaser liner and disposed between the first and second fillable spaces. The skin therapy system further includes a therapeutic composition contained within the first and second fillable spaces.

8 Claims, 16 Drawing Sheets

Related U.S. Application Data

(60) Provisional application No. 62/830,196, filed on Apr. 5, 2019, provisional application No. 62/505,700, filed on May 12, 2017.

(56) References Cited

U.S. PATENT DOCUMENTS

| | | | | |
|---|---|---|---|---|
| 5,050,596 | A * | 9/1991 | Walasek et al. | A41D 19/0068 2/158 |
| 8,613,732 | B2 * | 12/2013 | Montrose | A61K 8/31 604/290 |
| 2001/0048936 | A1 * | 12/2001 | Prenovitz | A61K 9/70 424/443 |
| 2002/0017310 | A1 * | 2/2002 | Gruenbacher et al. | A47L 13/18 132/320 |
| 2005/0202068 | A1 * | 9/2005 | Hasenoehrl et al. | A47K 7/03 424/443 |
| 2007/0206984 | A1 * | 9/2007 | Fagel et al. | C11D 17/049 401/7 |
| 2009/0149925 | A1 * | 6/2009 | MacDonald et al. | A61F 7/034 607/96 |
| 2010/0065081 | A1 * | 3/2010 | Vracknos | A61F 7/034 132/320 |
| 2012/0191023 | A1 * | 7/2012 | Young | B32B 5/024 601/18 |
| 2013/0096515 | A1 * | 4/2013 | Montrose | A61K 8/31 604/290 |

\* cited by examiner

SKIN THERAPY SYSTEMS

CROSS-REFERENCES TO RELATED APPLICATIONS

This application claims priority to U.S. Provisional Patent Application Ser. No. 62/830,196, filed on Apr. 5, 2019, and is a Continuation-In-Part of U.S. application entitled SKIN THERAPY SYSTEMS, assigned application Ser. No. 15/979,459, filed on May 14, 2018, which claims priority to U.S. Provisional Patent Application Ser. No. 62/505,700, filed on May 12, 2017, which are hereby incorporated by reference in their entirety. To the extent that the present disclosure conflicts with the referenced applications, however, the present disclosure is to be given priority.

BACKGROUND

Wax-based therapeutic compositions applied externally to the skin may be used to condition and soften skin, relieve joint pain, and improve a variety of skin conditions. Wax-based therapeutic compositions may be heated to melt the wax and to heat the skin or body part to which it is applied for pain relief. Current methods of melting bulk quantities of wax-based therapeutic compositions may take approximately two to three hours, impeding the delivery of the therapy to a person. Further, repeated heating-cooling cycles of wax-based therapeutic compositions for skin therapy may reduce the effectiveness of the composition over time. Additionally, overheating and uneven heating and cooling of the wax-based therapeutic compositions poses a significant safety risk for burning the person's skin.

SUMMARY OF THE TECHNOLOGY

A convenient and hygienic skin therapy system comprising an encaser, one or more therapeutic compositions, a sealing means and optional accessories is disclosed. A method of using such a skin therapy system is also provided. The skin therapy system and the use thereof provides an effective, efficient and safe therapeutic approach.

BRIEF DESCRIPTION OF THE DRAWING

A more complete understanding of the present technology may be derived by referring to the detailed description when considered in connection with the following illustrative figures. In the following figures, like reference numbers refer to similar elements and steps throughout the figures.

The figures described are for illustration purposes only and are not intended to limit the scope of the present disclosure in any way. Various aspects of the present technology may be more fully understood from the detailed description and the accompanying drawing figures, wherein.

DETAILED DESCRIPTION

Figure 1:
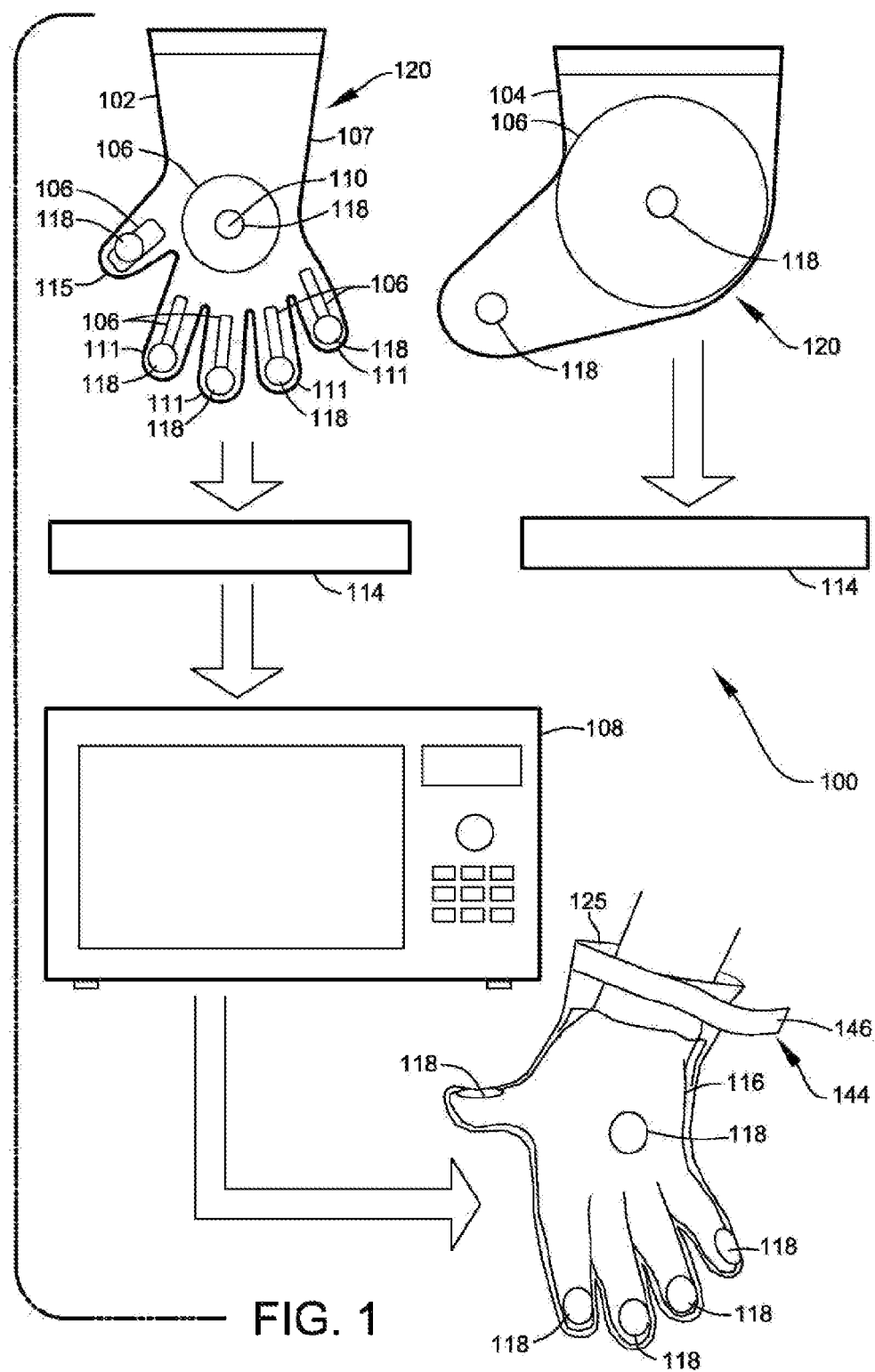
FIG. 1 illustrates an exemplary therapy system comprising a glove.

The present technology may be described in terms of functional block components and various processing steps. Such functional blocks may be realized by any number of components configured to perform the specified functions and achieve the various results. For example, methods and systems according to various aspects of the present technology may employ various materials for containing heat-stable therapeutic compositions which may be practiced in conjunction with any number of compositions and procedures for treating pain and inflammation of joints and other body parts and the systems described are merely exemplary applications for the technology. Various representative implementations of the present technology may be applied to any portion of the human body for the treatment of skin, pain, injury, and/or inflammatory medical conditions.

The particular implementations shown and described are illustrative of the technology and its best mode and are not intended to otherwise limit the scope of the present technology in any way. For the sake of brevity, conventional manufacturing, connection, preparation, sterilization, and other functional aspects of the system may not be described in detail. Furthermore, the connecting lines shown in the various figures are intended to represent exemplary functional relationships and/or steps between the various elements. Many alternative or additional functional relationships or physical connections may be present in a practical system.

Various aspects of the exemplary embodiments provide methods, apparatus, and systems for making and using a skin therapy system 100 and may comprise one or more of an encaser 120, encaser liner 116, therapeutic composition 106, and/or temperature indicator 118. The encaser 120 comprises an internal volume for receiving a person's body part, such as a hand, foot, and/or elbow. The encaser 120 may comprise a fastener that may be configured to attach or hold the encaser 120 to the desired portion of the body. The encaser liner 116 forms a second internal volume for receiving the body part and is positioned within the internal volume of the encaser 120 and helps with the substantially even distribution of the therapeutic composition 106 throughout the encaser 120 in a space formed between an inner surface of the encaser 120 and an outer surface of the encaser liner 116. The therapeutic composition 106 may comprise a wax with any number of cosmetic and/or pharmaceutical compositions that may treat problems of the skin and/or pain, injury, and/or inflammation of the body. The temperature indicator 118 may comprise any temperature activated device, ink, or other indicator that may be applied to the encaser 120, the encaser liner 116, and/or the therapeutic composition 106 that functions to indicate the temperature of the therapeutic composition 106 to ensure safe use of the therapy system. A detailed description of various embodiments is provided as a specific enabling disclosure that may be generalized to any application of the disclosed systems and methods.

Various embodiments of the skin therapy system 100 may be configured as a sealed, reusable container for a therapeutic composition 106 disposed inside the encaser 120. For example, an outer peripheral edge of the encaser liner 116 may be coupled to an inner surface of the encaser 120 along an outer peripheral edge of the encaser 120 such that the encaser liner 116 retains the general shape of the encaser 120 while also creating a fillable space or region between an inner surface of the encaser 120 and the outer surface of the encaser liner 116. The therapeutic composition 106 may then be disposed within the fillable space prior to use. The encaser liner 116 remains stretched to edges of the encaser 120 regardless of the composition and/or temperature of the therapeutic composition 106. This configuration prevents the contraction, or "balling up" of the encaser liner 116 when the body part is removed from the encaser 120 and/or when the therapeutic composition 106 cools after use.

The sealed configuration of the skin therapy system 100 allows it to be heated in a variety of apparatus while avoiding contamination of the enclosed encaser liner 116 and therapeutic composition 106. In today's clinical and/or cosmetic settings, such as hospitals, spas, and cosmetology salons, infection from methicillin-resistant *Staphylococcus aureus* (MRSA) can be deadly for patients and clients. Unlike conventional wax treatment systems, the encaser liner 116 is not dipped into a communal container of liquid paraffin (sometimes referred to as a "paraffin pot"). Instead, the fillable space is filled with the therapeutic composition 106 and sealed into place.

The encaser 120 may be formed into the shape of a desired body part such as: a hand, a foot, an elbow, a knee, a patch or strip suitable to attach to the torso or skull, and/or any other body part. Alternatively, the encaser 120 may be formed in the shape of a glove, a mitten, a muff, a fingerstall, a sock, a slipper, a shoe, a booty, a bonnet, a strip, a knee support, a skullcap, and/or a mask in the form of all or part of the face or head, or any other suitable forms and shapes. In one embodiment, the encaser 120 is hand shaped. In another embodiment, the encaser 120 is foot shaped.

The encaser 120 may comprise any suitable encaser materials to contain the therapeutic composition 106 such as carbon-fiber, plastic, transparent/translucent polymer such as polyethylene, plastic film, metal foil, depending on design requirements and heating sources. The encaser 120 may be made of elastic material that allows for expanding or stretching. The material used to make the encaser 120 is heat-durable and does not release toxic chemicals upon heating.

The material of the encaser 120 may be formed of at least two layers of the encaser material. For example, the encaser material may be adhered together to appear as a single layer. In some embodiments, a temperature indicator 118 such as a thermochromatic material comprising ink and/or other markings such as a trademark may be printed, stamped, and/or adhered to one layer of the encaser material. The encaser material may then be adhered to another layer of encaser material such that the thermochromatic material or other marking may be sealed between the two layers of the encaser material.

The encaser 120 may also be configured to accommodate body parts suffering from injury or restricted movement. For example, the encaser 120 may be formed for a hand in which the user may not have full range of motion or restricted movements in the fingers such that the fingers may not be comfortably placed in a standard glove configuration. In this embodiment, the encaser 120 may accommodate two or more fingers in a single section while allowing one or more other fingers to be positioned within their own section. The encaser 120 may also comprise elements, such as a strap, configured to help position a finger or body part in a desired position during treatment.

In some embodiments, the body part shaped encaser 120 may be unisized, such that it references to the average body part size acceptable in the industry. In one embodiment, the encaser 120 may be unisized for women's hands or feet. In one embodiment, the encaser 120 may be unisized for men's hands or feet. In one embodiment, the encaser 120 may be stretchable such that it can fit for any size of body part of a man and/or a woman. The encaser 120 may also be manufactured in a series of sizes that are standard in the industry, such like the standard sizes for gloves, shoes, and other similar products. The encaser 120 may have in-folds, which provide a three-dimensional shape that better accommodates the shape and dimension of a body part upon usage. In one embodiment, the encaser 120 is foot-shaped, with an in-fold providing a sole of a slipper, a boot, a shoe when unfolded.

FIG. 1 shows a schematic diagram depicting multiple embodiments of a single-use body part-shaped encaser 120 to exemplify the skin therapy system 100. Single-use body part-shaped encaser 120 utilizes at least one single-use glove 102 or, alternately, at least one single-use boot 104. Such a single-use glove 102 or single-use boot 104 comprises a hand or foot encaser 120 for encasing at least one human hand or foot. Each single-use glove 102 or each single-use boot 104, contains at least one therapeutic composition 106, which may be quickly heated (from about one to about four minutes) by various heating sources including, but not limited to, a microwave oven 108.

In some embodiments, each single-use glove 102 or single-use boot 104 is structured and arranged to be a sanitary one-time-use disposable product as further described herein. Upon reading this specification those of ordinary skill in the art will appreciate that, under appropriate circumstances, other device configurations, such as, for example, arm wraps, leg wraps, etc., may suffice. Various embodiments of skin therapy system 100, as described herein, may function to warm the skin to help soften dead skin (thus facilitating exfoliation). In addition, various embodiments of skin therapy system 100 may function to warm joints and assist with circulation.

Figure 2:
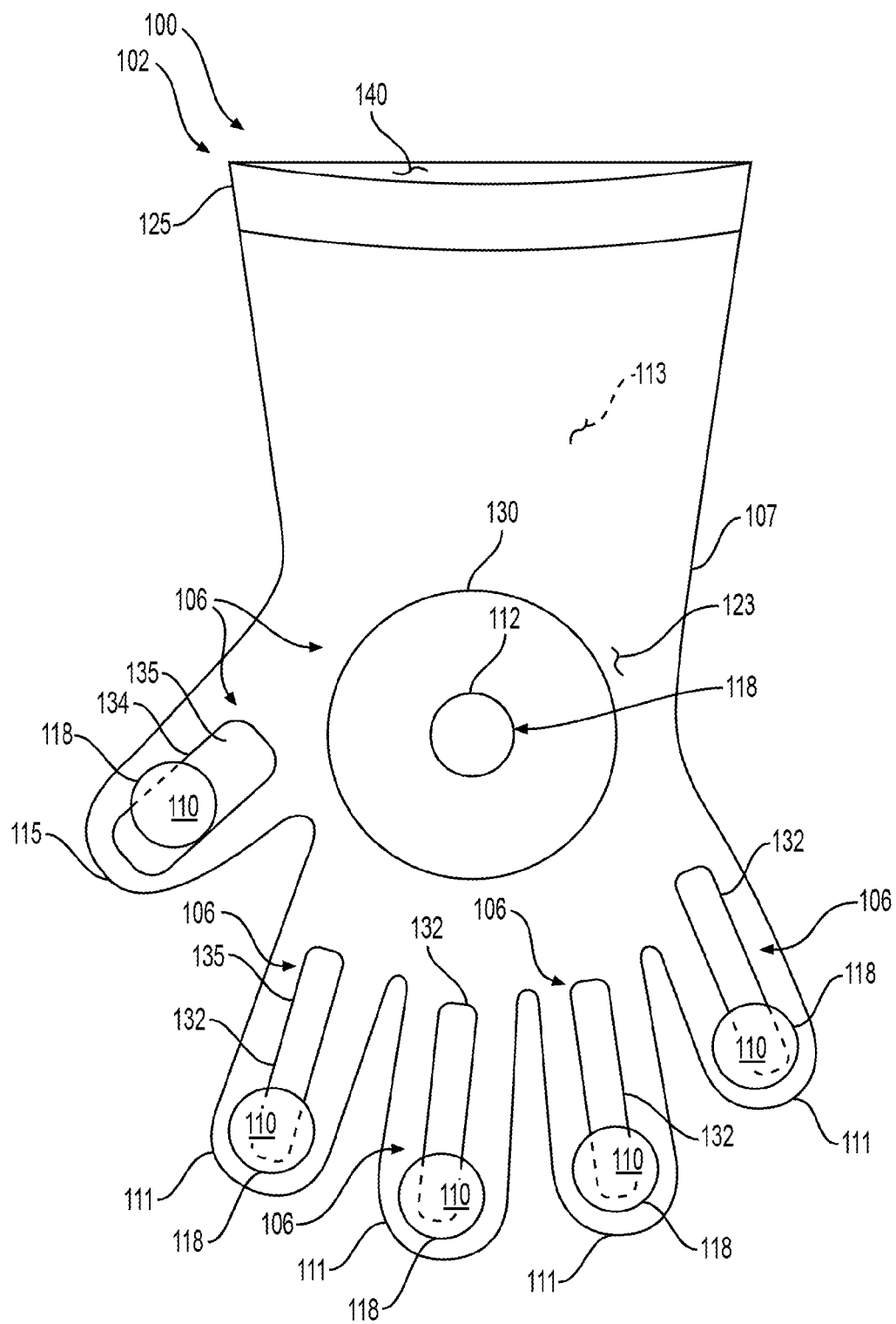
FIG. 2 shows a top view illustrating the therapy system comprising a glove.

As an example, FIG. 2 shows a top view, illustrating a single-use glove 102 of the skin therapy system 100. Single-use glove 102 may comprise therapeutic composition 106 positioned in each finger portion 111 and thumb portion 115 and at the palm region 123, as shown. In one embodiment, the palm region 123 of single use glove 102 comprises at least one first quantity of therapeutic composition 106. As shown in FIG. 2, the therapeutic composition 106 is placed within the interior of the single-use glove 102 in the palm region 123. In another embodiment, each single-use glove 102 comprises at least one second quantity of therapeutic composition 106 placed within the interior of the glove in each of the finger portions 111 and thumb portion 115, as shown. The therapeutic composition 106 in the palm region and the hand digit portions 111 and 115 may be the same or different.

As shown in FIG. 2, single-use glove 102 comprises one substantially flexible containment wall 107 having an interior portion 113 structured and arranged to contain at least one palm composition 130, a finger composition 132, and a thumb composition 134. Containment wall 107 further comprises an access opening, which is a hand aperture 140 in the single-use glove 102 embodiment. Hand aperture 140 may permit a user to insert a hand into the single-use glove 102, during use. Hand aperture 140 may comprise a width, when flat, of about seven inches. Single-use glove 102 may further comprise at least one temperature indicator 118, optionally positioned at any finger-tip, at the thumb-tip, at the palm area, or anywhere the temperature indicator 118 may sense the temperature of the therapeutic composition 106 enclosed in the single-use glove 102.

Figure 3:
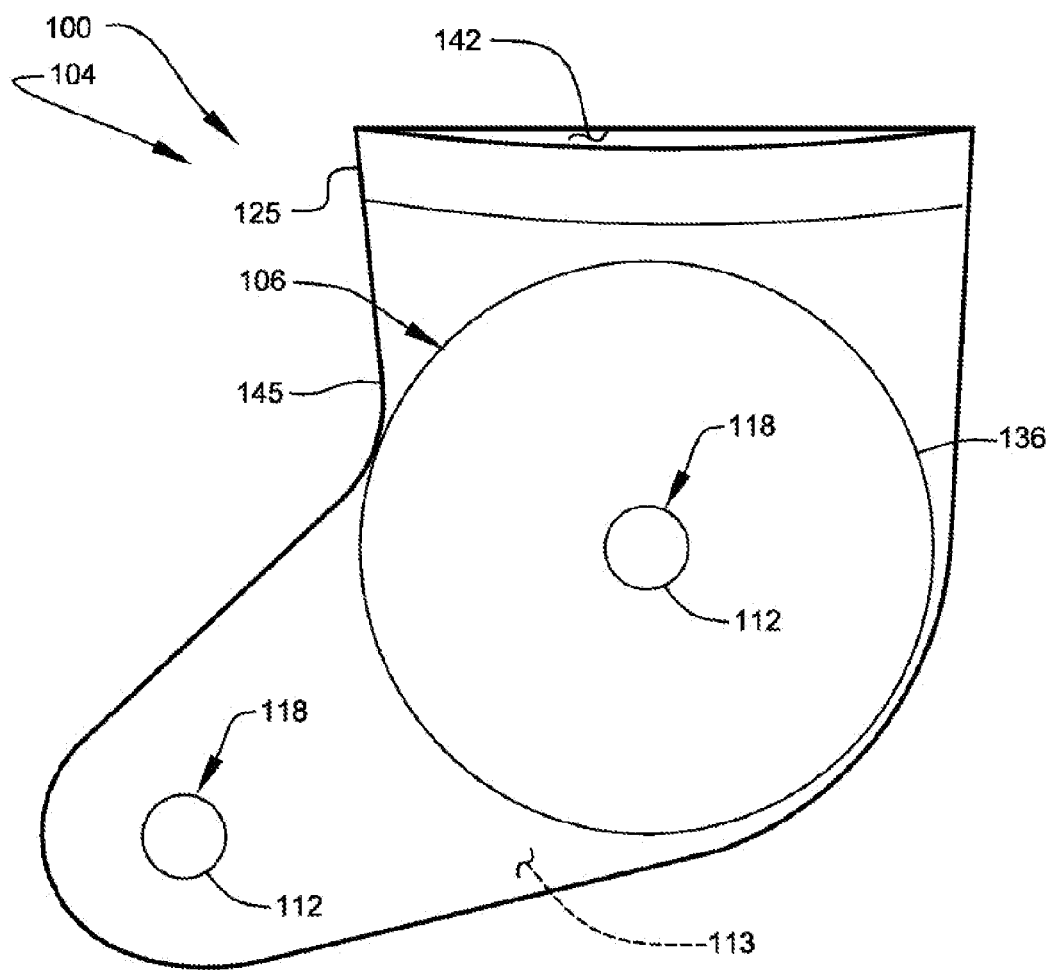
FIG. 3 illustrates an exemplary therapy system comprising a boot.

FIG. 3 shows a top view illustrating a single-use boot 104 of the skin therapy system 100. In one embodiment, the single-use boot 104 comprises a therapeutic composition 106 positioned in the ankle region 145, and/or toe region, of the single-use boot 104. Therapeutic composition 106 in ankle region 145 of single-use boot 104 may comprise at least one ankle composition 136. In addition, the single-use boot 104 comprises at least one foot aperture 142. Foot aperture 142 permits the user to insert a foot into the single-use boot 104, during use. Foot aperture 142 may comprise a width, when flat, of about ten inches.

Figure 11A:
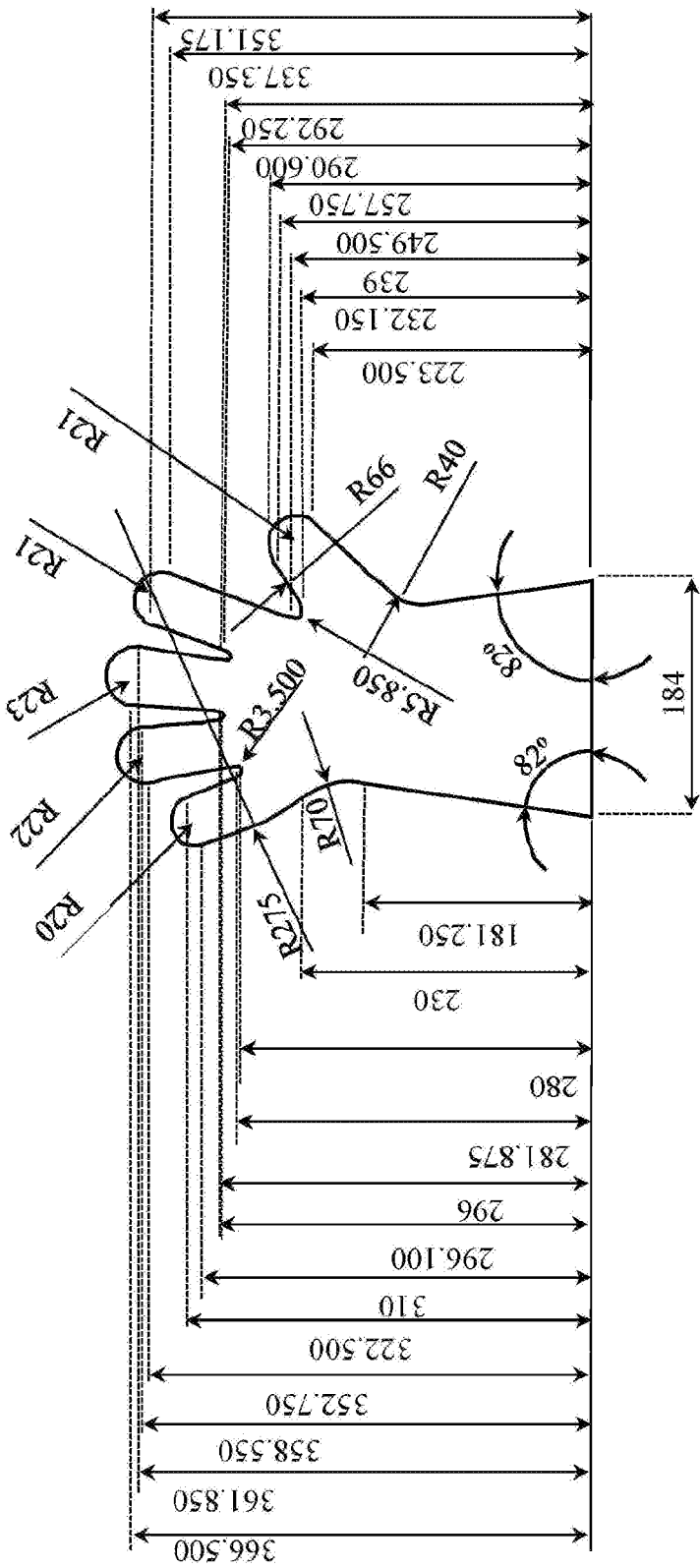
FIGS. 11A and 11B show additional dimensions and details of the therapy system comprising a glove and a boot.
Figure 11B:
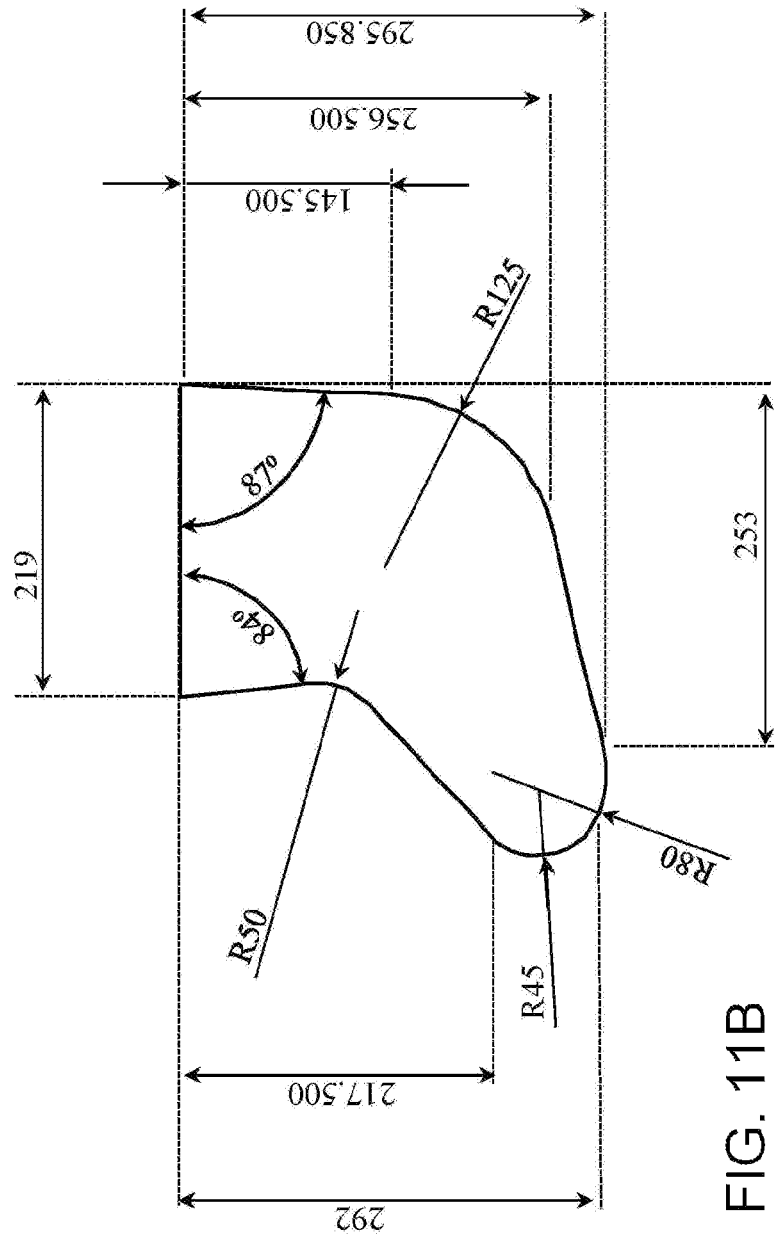

FIGS. 11A and 11B depict exemplary dimensions and details of an embodiment of a single-use glove 102 and single-use boot 104 for the skin therapy system 100. Upon reading this specification, those with ordinary skill in the art will now appreciate that, under appropriate circumstances, considering such issues as design preference, user preferences, marketing preferences, cost, structural requirements, available materials, technological advances, etc., other glove and boot material arrangements that meet or exceed criteria set forth herein may suffice. In addition to customized manufacturing a single-use glove 102 and single-use boot 104 encaser, the single-use boot 104 (without any therapeutic composition) is also commercially available for purchase, for example, the Sani-boot made by Keystone, or similar products through Pro-safety of Milwaukee Wis.

The therapeutic compositions 106 applicable for the skin therapy system 100 may be wax-based, liquid-based, or gel-based; all of which are to be spread evenly inside the encaser in a pre-determined amount prior to skin application. For a wax-based composition, the solidified composition is spread into a thin layer in a body part shaped encaser 120 with the shape essentially the same as the encaser 120. For a liquid based composition, a predetermined amount of the composition sufficient to cover targeted skin area is enclosed in a body part shaped encaser. The therapeutic composition 106 is contained inside the encaser 120 without the risk of leaking, spill, evaporation, or cross-contamination, and can readily be applied to the skin area without the need of further spreading while providing nearly even and direct contact to skin under treatment. The therapeutic compositions 106 applicable for the skin therapy system 100 may comprise various ingredients, which are selected according to their physical, chemical, or pharmaceutical characteristics suitable for the skin therapy system 100 and therapeutic targets. The wax-based, liquid-based, or gel-based therapeutic composition 106 is pre-packaged into the encaser of the skin therapy system 100 and may or may not require heating prior to skin application. In other embodiments, the wax-based, liquid-based, or gel-based therapeutic composition may be installed into the encaser 120 customarily prior to a therapy session. The written description below provides further details of therapeutic compositions 106.

Each encaser 120 of the skin therapy system 100 may comprise one or more therapeutic compositions 106. In some embodiments, the therapeutic composition 106 is positioned in a single-use body part shaped encaser 120 at time of manufacturing. In some embodiments, the therapeutic composition 106 is uniformly positioned in a single-use body part shaped encaser 120, such that the therapeutic composition 106 is spread about evenly as a thin layer throughout the encaser 120. In some embodiments, the therapeutic composition 106 in a body part shaped encaser 120 is a contiguous thin layer of solidified or gel-like form extending evenly to the interior portion 113 or region of an encaser 120. Depending on the therapeutic composition 106 (solid or gel, wax-, mud- or clay-based mixture), the thickness of the contiguous thin layer of the composition may be between about 0.1 inch to about 1.5 inches. In some embodiments, a solid form therapeutic composition 106 of a quantity may be molded into a certain shape of certain size before positioned in a body part shaped encaser 120. In other embodiments, the therapeutic composition 106 of a quantity may be added in to a body part shaped encaser 120 when the therapeutic composition 106 is in a liquefied state, which then may solidify or undergo gelification with or without pressing or molding the composition into the shape of the encaser 120 upon cooling or sitting. Upon reading this specification, those with ordinary skill in the art will now appreciate that, under appropriate circumstances, considering such issues as design preference, user preferences, marketing preferences, cost, structural requirements, available materials, technological advances, etc., other therapeutic substance insert arrangements such as, for example, pre-coating of the internal glove, linked portions insertable into the glove, etc., may suffice.

In some embodiments a quantity of a first therapeutic composition 106 is placed in each of the fingers and thumb portion 111, 115 of a hand shaped encaser 120, and a quantity of a second therapeutic composition 106 is placed in the palm region 123 of a single-use body part shaped encaser 120; wherein the first therapeutic composition 106 heats up at a slightly slower rate than the second therapeutic composition 106 placed in the palm region 123 such that, upon heating, all of therapeutic composition 106 placed into a hand shaped encaser 120 will heat up or melt about equally and reach a predetermined temperature at about the same time. Even heating without overheating any portion of a therapeutic composition 106 may be important for even liquefaction of solid form therapeutic composition 106, and the safe use of the skin therapy system 100 to prevent skin injury due to excessive or uneven heat during the direct skin-composition contact in a skin therapy.

As exemplified in FIG. 2, therapeutic composition 106 in each finger portion 111 may comprise at least one finger composition 132, or alternately, in thumb portion 115 at least one thumb composition 134. Finger composition 132 may comprise enough therapeutic composition 106, when melted or heated, to substantially coat each finger portion 111 of single-use glove 102. In one embodiment, finger composition 132 comprises about one-half ounce of therapeutic composition 106. Thumb composition 134 may comprise enough therapeutic composition 106, when melted or heated, to substantially coat the thumb portion 115 of single-use glove 102. In one embodiment, thumb composition 134 comprises about one ounce of therapeutic composition 106. In one embodiment, finger composition 132 and thumb composition 134 comprise at least one insert 135, which may be a bar as shown, or pellets, or a thin layer of solidified or gel like therapeutic composition 106. In one embodiment, finger composition 132 comprises an insert 135 such as a bar having a length of about three inches, a width of about one-half inch, and a thickness of about one-half inch. In one embodiment, thumb composition 134 comprises an insert 135 such as a bar having a length of about two-and one-half inches, a width of about one inch, and a thickness of about one-half inch.

Therapeutic composition 106 in the palm region 123 comprises at least one palm composition 130. Palm composition 130 may comprise enough therapeutic composition 106, when melted or heated, to substantially coat the palm region 123 of single-use glove 102. In one embodiment, palm composition 130 comprises at least one insert of the therapeutic composition 106, which may be in a form of a circular disc, as shown, or a bar, or pellets, or an evenly spread out solidified or gel like thin layer. In one embodiment, palm composition 130 comprises two-and-one-quarter ounces of therapeutic composition 106. In one embodiment, palm composition 130 in a form of circular disk comprises a diameter of about four inches, and a thickness of about one-half inch.

As exemplified in FIG. 3, the therapeutic composition 106 in ankle region 145 of single-use boot 104 may comprise at least one ankle composition 136. In one embodiment, ankle composition 136 comprises enough therapeutic composition 106, when melted, to substantially coat single-use boot 104. Ankle composition 136 may comprise about six ounces of therapeutic composition 106. In one embodiment, ankle composition 136 is in a form of at least one insert, which may be a circular disc, as shown, or a bar, or pellets, or an evenly spread out solidified or gel like thin layer. The ankle composition 136 in a form of circular disc comprises a diameter of about eight inches and a thickness of about one-quarter inch. In some embodiments, the therapeutic composition 106 is inserted as a contiguous thin layer of solidified or gel like form extending evenly throughout the ankle region 145, a toe portion of the encaser 120 and up to a bottom of an upper section 125 proximate foot aperture 142.

Hand aperture 140 or foot aperture 142 may be sealed or partially sealed to prevent spilling of therapeutic composition 106 outside of the body part shaped encaser 120 during heating and application. In some embodiments, the apertures 140 and 142 are sealed by folding, a tongue in groove locking mechanism, removable tape or adhesive strips, removable adhesive, sewing, iron-on or heat seals, such that air or steam in the encaser may be released when the seal is removed and the encaser 120 is heated. In some embodiments, the apertures 140 and 142 are partially sealed to permit venting of any accumulated gases associated with heating of therapeutic composition 106. Other venting arrangements such as, for example, one-way vents, slits, re-sealable portals, etc., may also be applicable. In some embodiments, the apertures 140 and 142 are vacuum sealed, such that the encaser 120 stays air-free during heating so that heat and moisture in the encaser are retained, and the explosion or expanding of the encaser 120 during heating can be avoided. The seal of a body part shaped encaser 120 may be removed by cutting, trimming, or tearing after heating and prior to skin application.

Figure 4A:
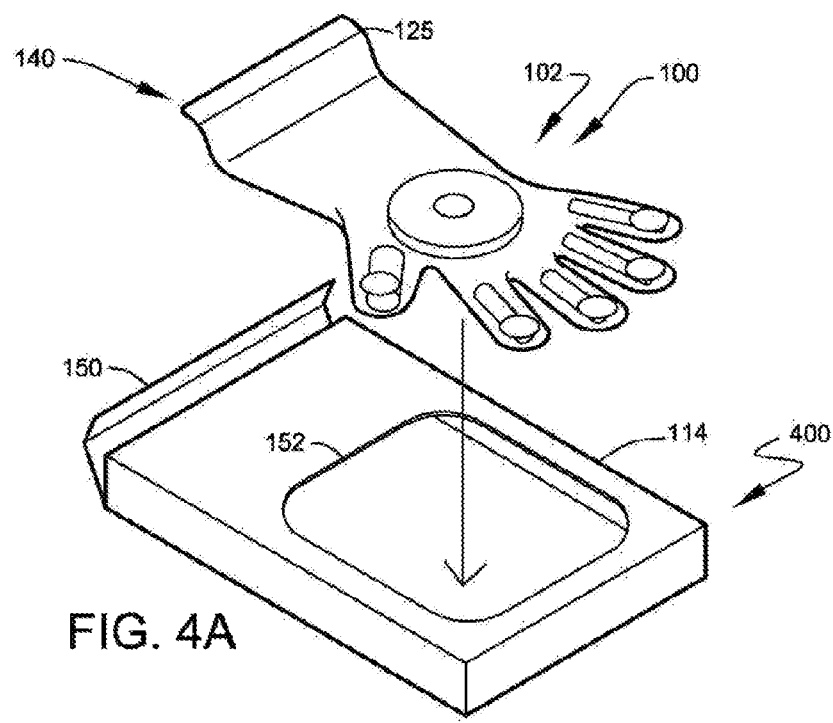
FIG. 4A shows a perspective view illustrating a container for holding and heating the therapy system.
Figure 4B:
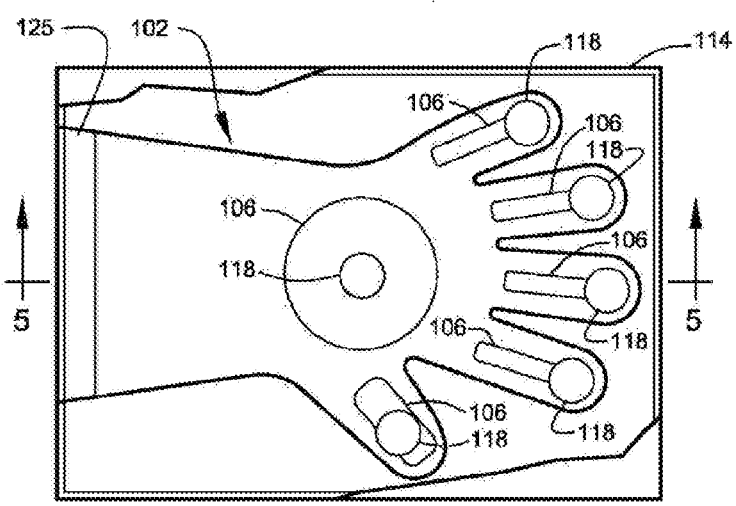
FIG. 4B shows a planar view illustrating the container for holding and heating of the therapy system.
Figure 5:
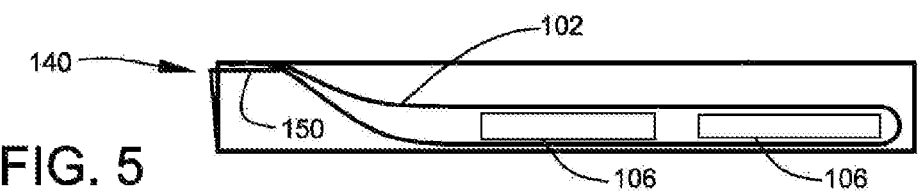
FIG. 5 shows a cross-sectional view along section 5-5 of FIG. 4B.
Figure 6A:
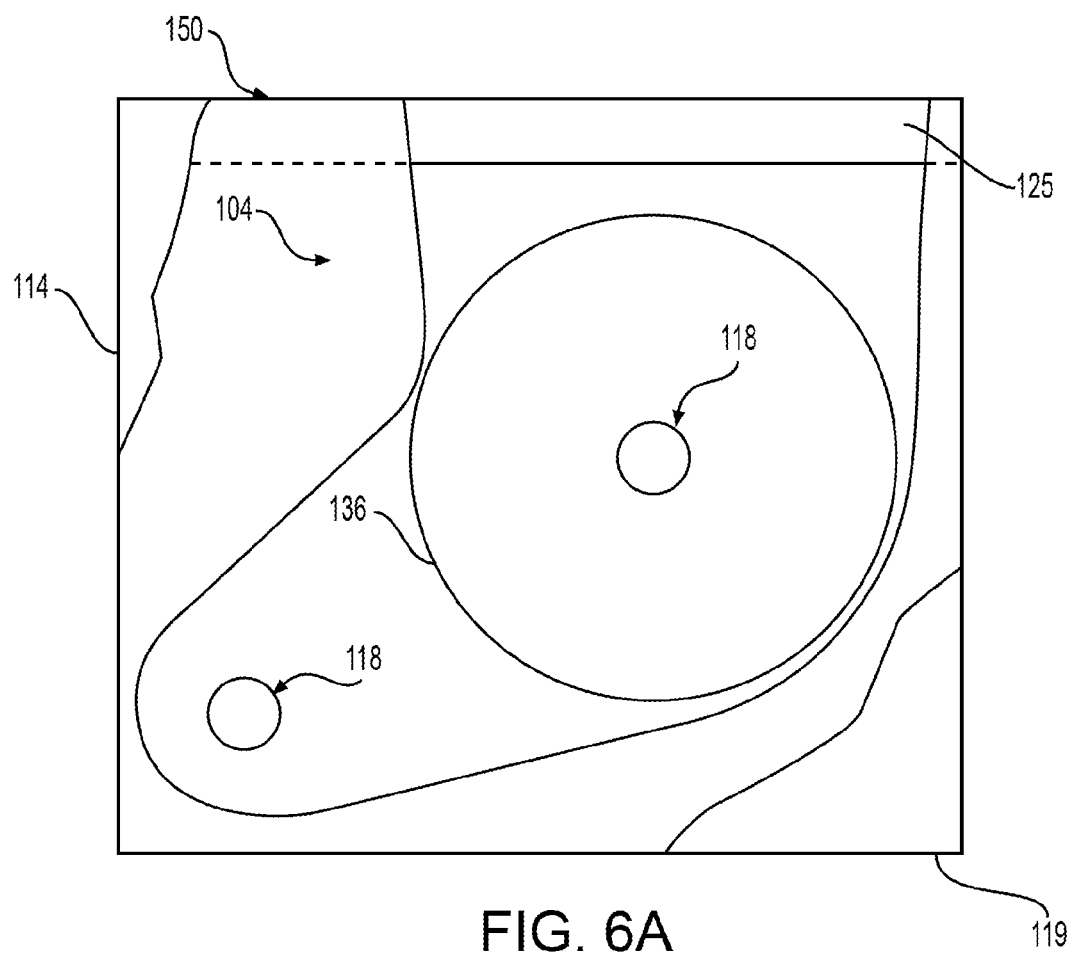
FIG. 6A shows a planar view illustrating the container for holding and heating the therapy system.

In other embodiments, a closure 150, as best shown in FIGS. 4A-6A, of a sealing box 114 may be used to hold and seal hand aperture 140 and foot aperture 142 (shown in FIG. 6A). The upper section 125 of the gloves 102 and boots 104 may have an extended length along respective wrist (glove) and ankle (boot) portions as shown in FIG. 2 and FIG. 3. Once therapeutic composition 106 is positioned in single-use wax-based encaser 120, each device may be folded over on the opened end (aperture) and placed in the sealing box 114, with the folded portion of the aperture 140, 142 aligned with the flap of the closure 150 of the sealing box 114 as shown in FIGS. 4A, 4B and 5. The flap of the closure 150 is elevated with respect to the rest of single-use body part shaped device 120 when the closure 150 is in a closed position as shown in FIG. 5. The elevated position of the hand aperture 140 or foot aperture 142 provided by the elevated flap closure 150 when the sealing box 114 is closed seals the aperture 140, 142 and prevents spilling of therapeutic composition 106 outside of single-use body part shaped device 120 during heating by further utilizing gravity. Closure 150 also permits venting of any accumulated gases associated with heating of therapeutic composition 106.

The sealing box 114 may further comprise at least one window 152 in addition to at least one closure 150 (FIG. 4A). Window 152 permits viewing of temperature indicator 118 (described below), during heating, to visually determine the proper temperature. Window 152 also permits viewing therapeutic composition 106, during heating, to visually determine complete melting of therapeutic composition 106. Upon reading this specification, those with ordinary skill in the art will now appreciate that, under appropriate circumstances, considering such issues as design preference, user preferences, marketing preferences, cost, structural requirements, available materials, technological advances, etc., other viewing arrangements such as, for example, multiple smaller portals, multiple windows, slits, pop-up notifiers, sound notifiers, etc., may suffice.

In some embodiments, one or more single-use therapy encasers 120 is placed in one sealing box 114. In other embodiments, an individual single-use encaser 120 is placed in one sealing box 114. The sealing box 114 may be for single-use or may be used repeatedly. The external sealing box 114 can be microwavable. In some embodiments, the microwavable sealing box 114 may comprise at least one microwave-safe material selected from cardboard, a wood-pulp material, carbon-fiber, microwavable plastics, ceramics, wood derivative materials, and any combination thereof.

The encaser liner 116 is used to help apply the therapeutic composition 106 to the user's skin during treatment. For example, the encaser liner 116 may be configured to allow at least a portion of the therapeutic composition 106 to migrate from the fillable space through the encaser liner 116 itself and to the user's skin. The encaser liner 116 may have the same shape and dimension as the encaser 120 or be sized slightly smaller, such that the encaser liner 116 can be inserted into the encaser 120 with ease.

The encaser liner 116 may be made of material selected from paper, textile, non-woven fabrics, plastic fabrics, non-woven polypropylene fabrics, and any combination thereof. The encaser liner 116 may be opaque or may have any level of transparency and may have any tint of color. The addition of the encaser liner 116 provides a range of functions such as heat insulation, even heating, overheating spot prevention, moisture retaining, distribution, absorbency, resilience, stretch, softness, strength, cushioning, padding, filtering and sterility. Additionally, the encaser liner 116 provides a medium support or a holding agent for any form of the therapeutic composition 106 including, but not limited to, mud-based, clay-based, wax-based, liquid-based and gel-based compositions, such that the therapeutic composition 106 has reduced mobility within fillable space of the encaser 120. In one embodiment, the encaser liner 116 is made of paper sheet. In another embodiment, the encaser liner 116 is made of non-woven polypropylene fabric configured to allow one or more ingredients of the therapeutic composition 106 to migrate from the fillable space to the user's skin during use.

A single-use body part shaped encaser 120 may further comprise a temperature indicator 118 for visually indicating the temperature range of a therapeutic composition 106 during and after heating. This feature is provided to assist in preventing overheating of therapeutic composition 106 and to monitor the temperature of the skin therapy system 100 during the therapy. For example, 126° F. is a recognized temperature safety limit in the industry. A therapeutic composition 106 with a temperature above 126° F. is not suitable for direct application on top of skin. The temperature indicator 118 may be a coating 110, a strip, a sticker 112, a label, a tape, or any other form that is applicable. The temperature indicator 118 may be reversible or irreversible depending on the indications desired to be given. Single-use body part shaped encaser 120 comprises at least one temperature indicator 118. In some embodiments, the temperature indicator 118 comprises at least one thermochromatic coating 110 structured and arranged to visibly indicate internal therapeutic composition temperature of a respective body part shaped encaser 120 comprising therapeutic composition 106. In some embodiments, one or more temperature indicator 118 is located on the interior side of the encaser 120. In some embodiments, the temperature indicator 118 may be applied as a thermochromatic patch or sticker 112 to the exterior surface of the encaser 120. The temperature indicator 118 functions to visually indicate the approximate temperature of therapeutic composition 106 such that the user is warned if the temperature is above or under a desired range of temperature. In various embodiments, the visual indication may be through a change of color, the disappearance of color, the appearance of color, a showing of a number presenting a temperature, a level of temperature, a range of temperature, and/or other number or text that conveys information about the temperature to the user. Other temperature indicators may include pop-up notifiers or sound notifiers as known in the art.

In various embodiments, the single-use glove 102, as illustrated in FIG. 2, comprises at least one temperature indicator 118. The temperature indicator(s) 118 may be positioned anywhere on the surface of the encaser, including on each fingertip, at the thumb-tip, and at the palm area of single-use glove 102. Similarly, and referring to FIG. 3, the single-use boot 104 may also comprise at least one temperature indicator 118, positioned anywhere including at the ankle area and at the toe area of single-use boot 104. Both the thermochromatic coating 110 and the thermochromatic sticker 112 may change to at least one warning-temperature color, when therapeutic composition 106 exceeds at least one ideal temperature range. Upon reading this specification, those with ordinary skill in the art will now appreciate that, under appropriate circumstances, considering such issues as design preference, user preferences, marketing preferences, cost, structural requirements, available materials, technological advances, etc., other temperature arrangements such as, for example, greater or lesser temperatures, varying ranges of temperatures, more or fewer temperature indicators, etc., may suffice.

Figure 12A:
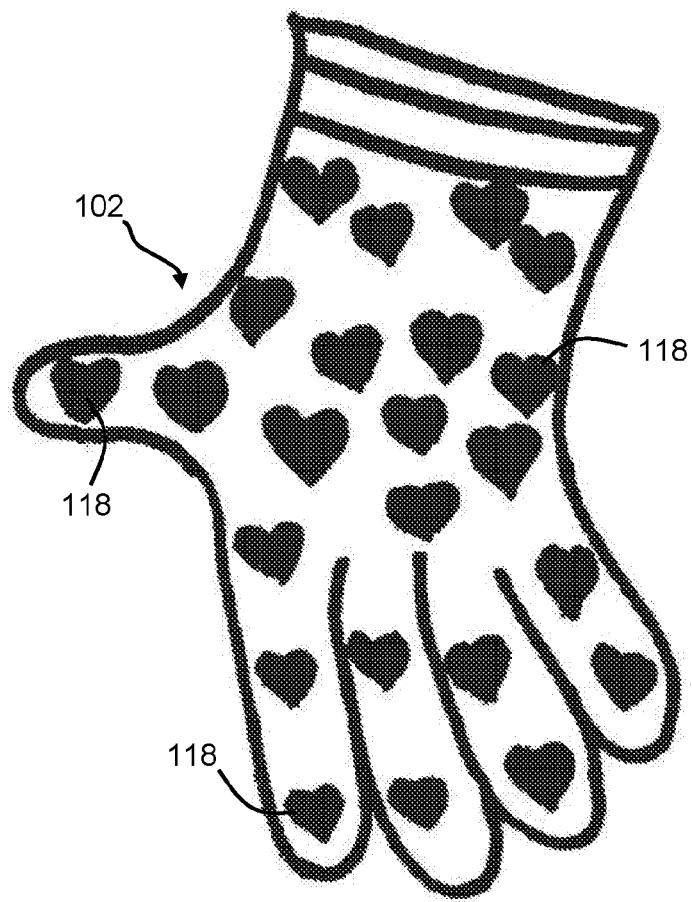
FIGS. 12A and 12B illustrate exemplary thermochromatic ink applied to the encaser of the therapy system.
Figure 12B:
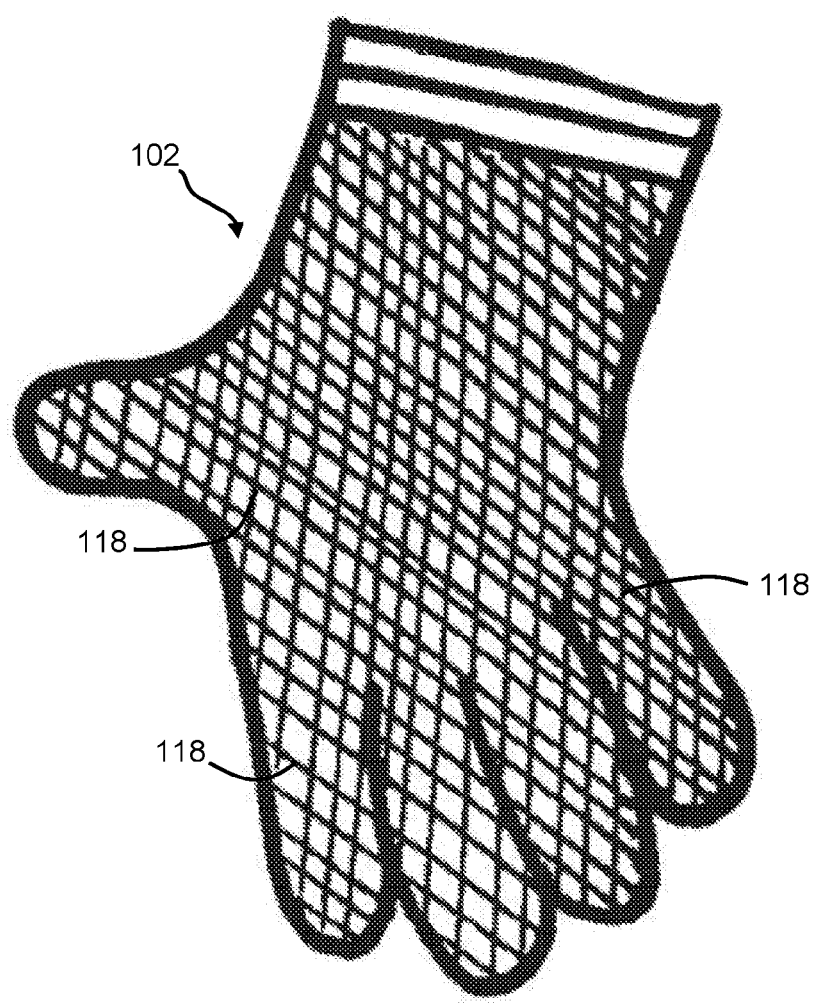
Figure 13:
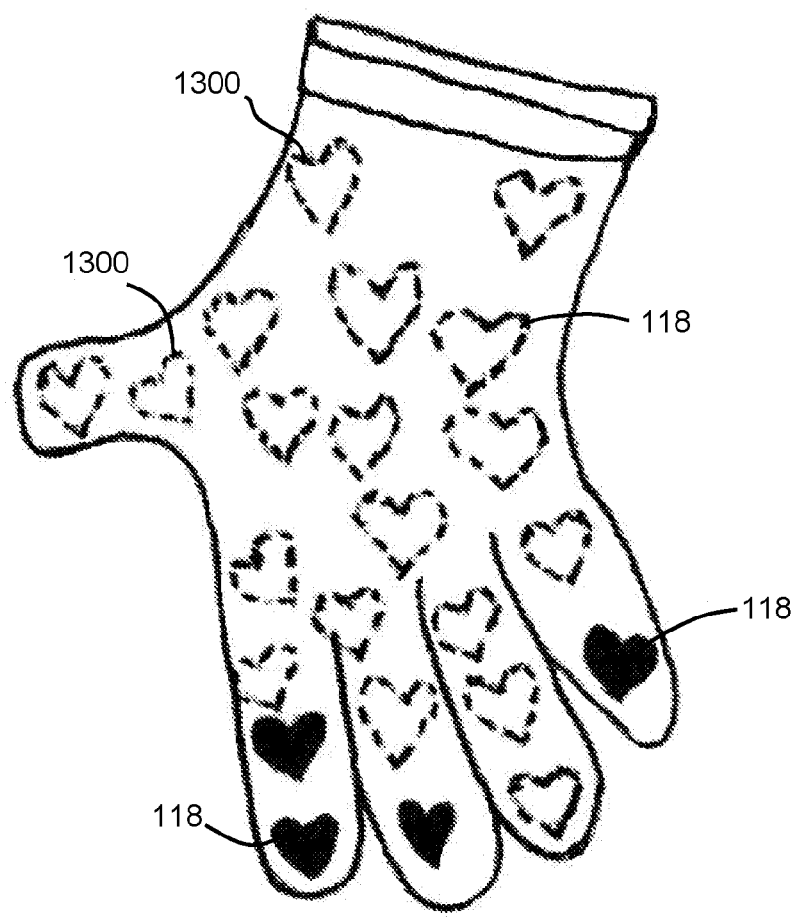
FIG. 13 illustrates a therapy system with thermochromatic ink indicating uneven heat in the therapeutic composition.

Referring to FIGS. 12A-B and 13, in various embodiments, the temperature indicator 118 may comprise a temperature activated ink. In various embodiments, the temperature activated ink may be sprayed, printed, stamped, and/or otherwise applied between two substrates of film that comprise the encaser 120. The two substrates of film may then be laminated together to form the material for the encaser 120. The use of the temperature indicator 118 comprising the temperature activated ink embedded between the two layers of laminated film that comprise the encaser 120 may allow the skin therapy system 100 to be heated in hot water baths in hospitals or other clinical setting and prevent the temperature activated ink from washing or fading away.

In some embodiments, as shown in FIG. 12A, temperature indicator 118 comprising the temperature activated ink may be applied onto the film in discrete patches, such as a design and/or trademark throughout the therapy system 100. FIG. 12B illustrates another embodiment in which the temperature activated ink may be applied evenly onto the film. A change in the color of the temperature indicator 118 may indicate that the therapeutic composition 106 inside the encaser 120 may be too hot for safe use and may cause burns to the skin. In that case, the user may allow the therapeutic composition 106 to cool to a safe temperature as indicated by a return of temperature indicator 118 to its previous color before applying the skin therapy system 100 to the skin. As shown in FIG. 13, uneven heating of the therapeutic composition 106 may become apparent to the user when the temperature indicator 118 has one color in some areas of the skin therapy system 100 and a different color 1300 (including no color) in other areas. This safety feature may be useful to users with insensitivity in their fingertips caused by nerve damage, diabetic neuropathy, and other conditions that render the user unable to feel their skin burn right away.

Once a single-use body part shaped encaser 120 comprising a therapeutic composition 106 is applied to the targeted skin area, a fastener may attach and stabilize the encaser to the skin area for a period of therapy time. The fastener may be chosen from adhesive tape, straps, strings, elastic material, fabric tape, tubing, or other functional devices. The fastener may or may not be included in the skin therapy system. In one embodiment, a body shaped encaser 120 comprises a fastener.

Figure 7:
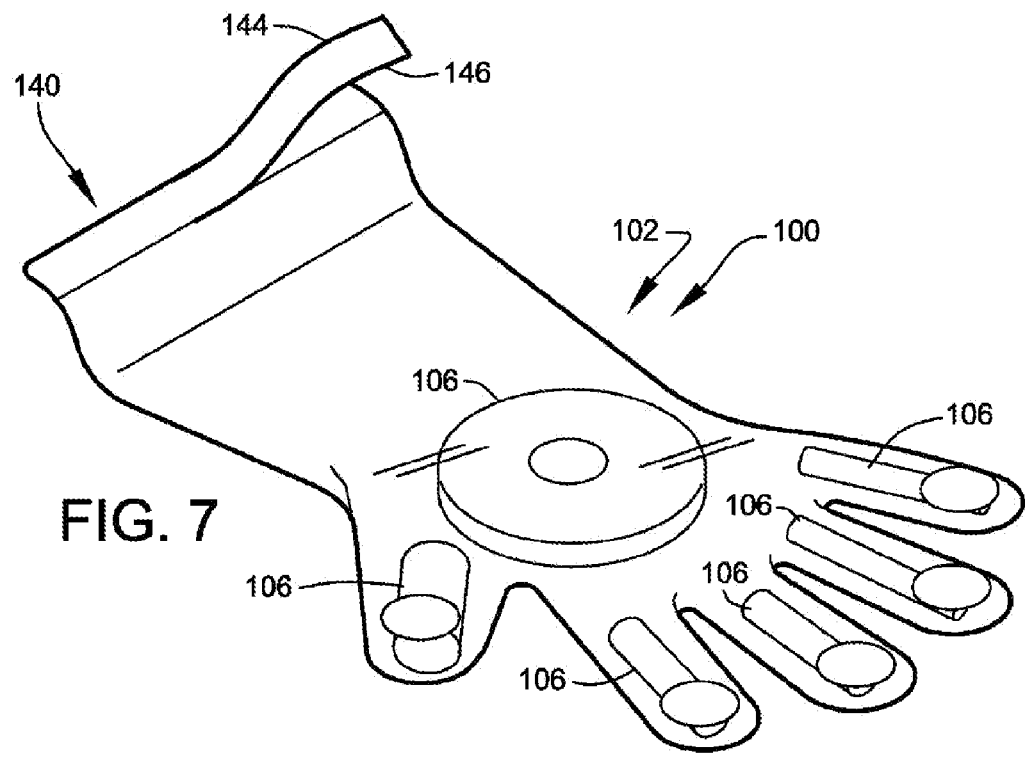
FIG. 7 shows a perspective view illustrating the therapy system comprising a glove.
Figure 9:
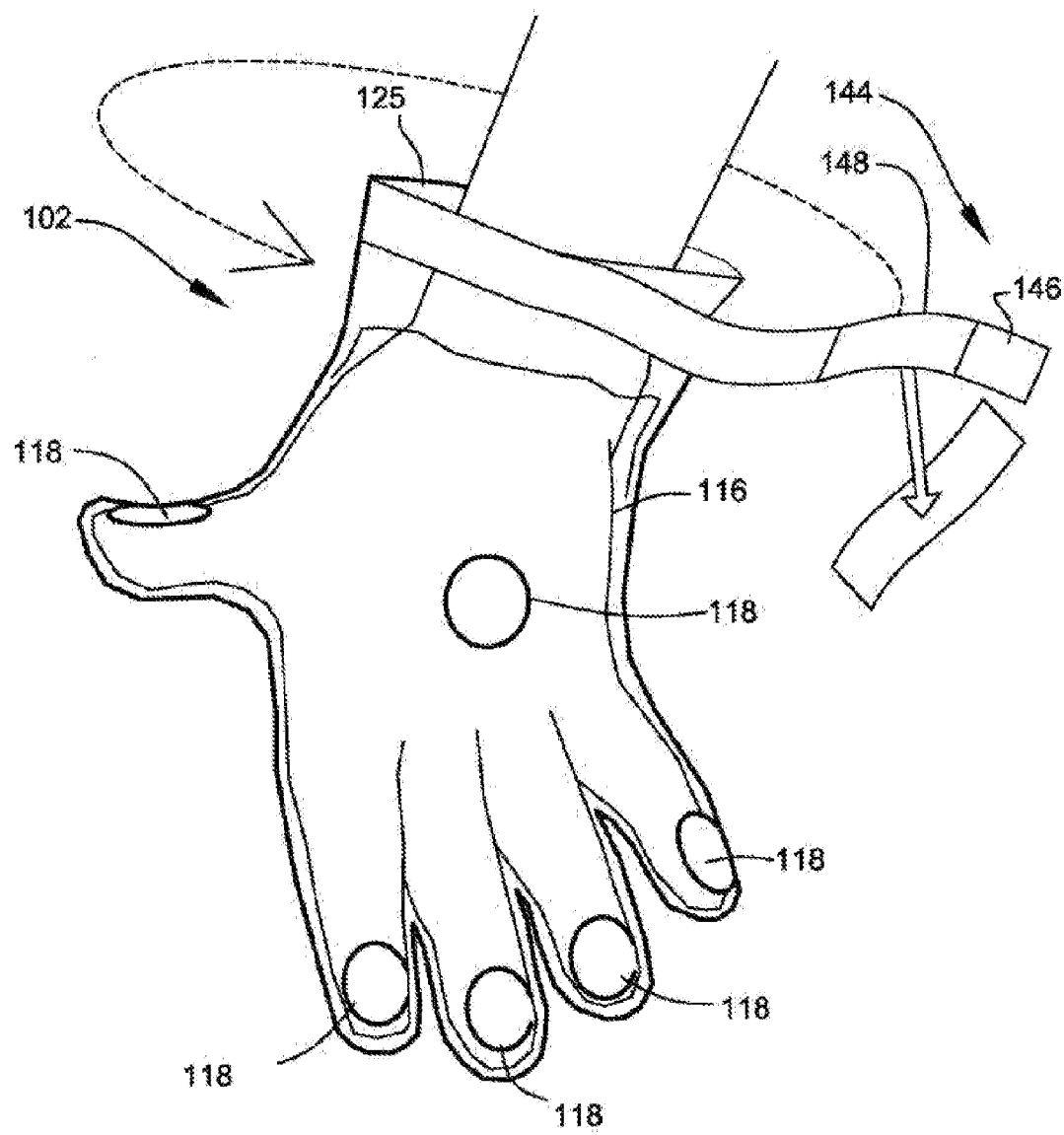
FIG. 9 illustrates a method of using the therapy system.

FIG. 7 shows a perspective view of an exemplary single-use glove 102 of the skin therapy system 100, and FIG. 9 shows a method using the single-use glove 102 wherein the single-use glove 102 comprises at least one aperture seal 144. In one embodiment, aperture seal 144 further comprises at least one strap 146, which includes at least one adhesive strip 148. In use, after a user inserts a hand, or alternately a foot, into single-use body part shaped encaser 120, strap 146 can be wrapped around and affixed to a wrist or an ankle using adhesive strip 148 to ensure attachment and stability of the skin therapy system 100 during therapy. Strap 146 and strip 148 may vary in width and length. In one embodiment, strap 146 has a length of about seven inches and a width of about one-half inch. In some embodiments, strap 146 is attached to single-use body shaped encaser 120 through at least one seam. Alternately, strap 146 may be attached to single-use body shaped encaser 120 by heat welding or mechanical fastener. In one embodiment, adhesive strip 148 comprises a length of from about one-half-inch to about four-inches.

The skin therapy system 100, as disclosed herein, may further comprise one or more external padding, outer pouch, coverlet, harness, heating or temperature maintaining element, stand-alone user instruction, or instruction attached to the single use body part shaped encaser. The instruction may be in a print, a writing, a disk, or any other suitable medium. In one embodiment, one or more heating or temperature maintaining elements is attached to the exterior surface of the body part shaped encaser of the skin therapy system 100.

Figure 14:
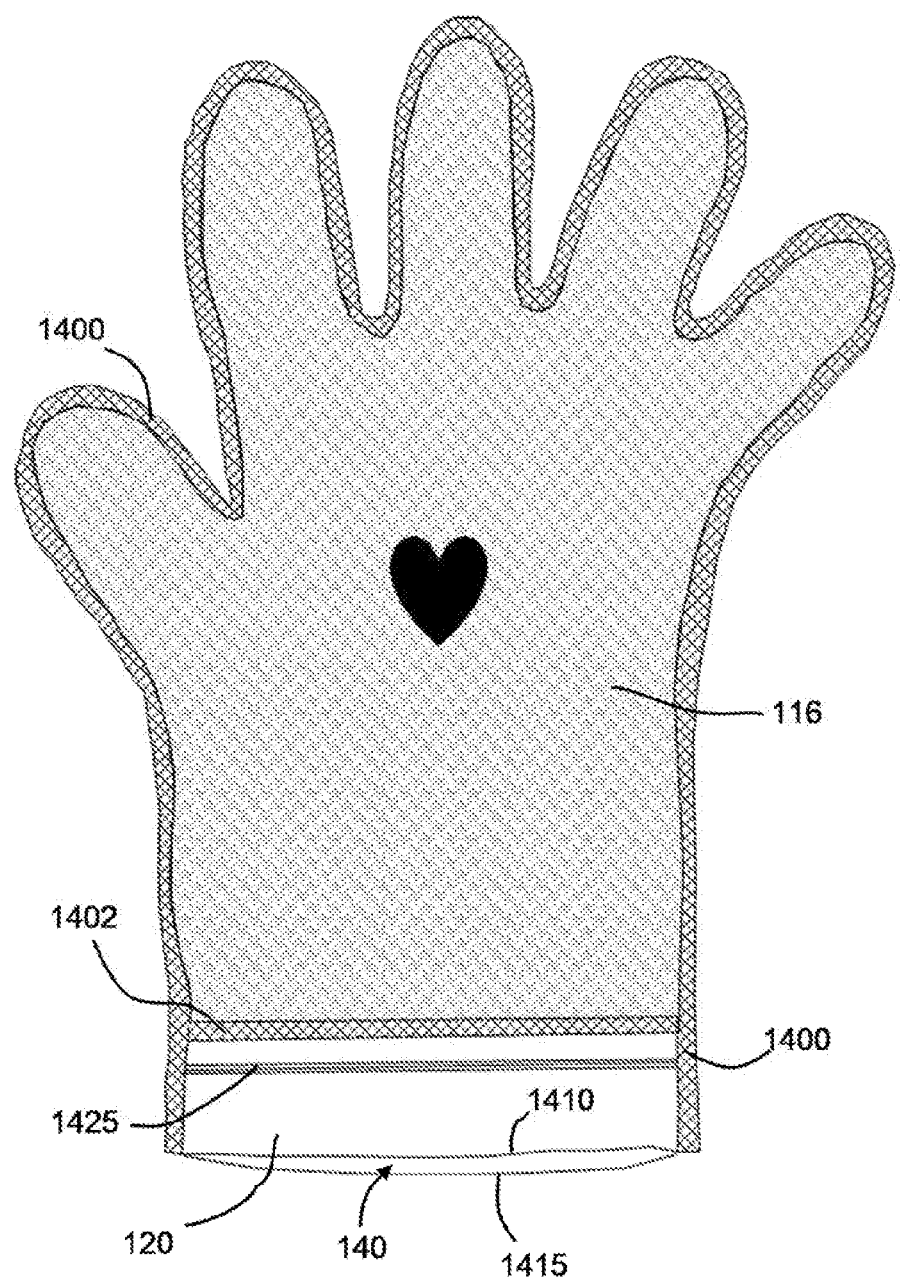
FIG. 14 illustrates an exemplary therapy system with heat-sealed edges.

Referring now to FIG. 14, the encaser liner 116 may be positioned between a first substrate of film 1410 and a second substrate of film 1415, which form the encaser 120. The encaser liner 116 may extend to the edges of the first substrate of film 1410 and the second substrate of film 1415. Outer peripheral edges of the encaser liner 116, the first substrate of film 1410, and the second substrate of film 1415 may be sealed together to form a first hermetic seal 1400 along the outer edges of the skin therapy system 100. This also forms the fillable space between an inner surface of the first and second substrates of film 1410, 1415 and the encaser liner 116. The fillable space may be filled with the therapeutic composition 106 and subsequently sealed in place with at least one additional hermetic seal 1402 positioned near a wrist portion of the encaser 120. The hermetic seals 1400, 1402 are used to keep the therapeutic composition 106 within the fillable space and around the encaser liner 116 during and between uses.

Access to the internal volume of the encaser 120 is accomplished via the hand aperture 140 that allows the user to insert their hand into the encaser liner 116. The hand aperture 140 may be positioned at an end most location of the encaser 120 to allow a user's hand to be inserted into and removed from the internal volume of the encaser 120 similar to a regular glove.

A closure element 1425 may be positioned between the hand aperture 140 and the additional hermetic seal 1402 to form a temporary seal to the internal volume of the encaser 120. For example, the closure element 1425 may comprise a tongue in groove closure and/or other suitable closure that can be used to reseal the encaser 120 between uses. This temporary seal may be used to help prevent moisture intrusion, bacterial contamination, and the accumulation of particulates within the internal volume.

The therapeutic composition 106 of the skin therapy system 100 may be solid, semi-solid or liquid at the room-temperature. In some embodiments, the therapeutic composition 106 is mud-based. In some embodiments, the therapeutic composition 106 is clay-based. In some embodiments the therapeutic composition 106 is wax-based, and the wax may be in a solid, semi-solid or liquid state. In some embodiments, therapeutic composition 106 does not comprise wax, and is mostly in a liquid state. The therapeutic composition 106 may be pre-packaged or packaged prior to the commencement of a therapy session such that it is enclosed in the body part shaped encaser 120 of the skin therapy system 100, as disclosed herein. Upon application, the targeted skin area is in direct contact with the therapeutic composition 106. The formulation of the therapeutic composition 106 may vary depending on the skin condition to be treated, therapeutic purposes, or specific portions of a body part shaped encaser 120 of the skin therapy system 100, for example, fingers versus palm, toes versus ankles.

Various embodiments of the therapeutic composition 106 of the skin therapy system 100 may comprise a hot lotion and/or a cold lotion. For example, the therapeutic composition 106 may comprise shea butter and/or any other moisturizer, emollient, and/or humectant suitable for improving the condition of the skin. In another embodiment, the therapeutic composition 106 may comprise glycolic acid for a glycolic peel of the skin.

Various embodiments of the therapeutic composition 106 of the skin therapy system 100 may comprise a wax-based composition. The wax may be selected from paraffin wax, soy wax, beeswax, and palm wax. In one embodiment, the therapeutic composition 106 is paraffin based. Paraffin utilized in the present embodiments may soften, hydrate and protect the skin and may also be used as a treatment for some skin disorders. The paraffin may be selected from paraffin wax, liquid paraffin oil (also called mineral oil, nujol, adepsine oil, alboline, glymol, medicinal paraffin, or saxol), semi-solid paraffin (also called petroleum jelly, petrolatum, white petrolatum or soft paraffin), and any derivatives thereof. The paraffin wax based therapeutic composition 106 has a melting point temperature in the range between about 46° C. and about 68° C., between about 44° C. and about 60° C., between about 42° C. and about 55° C., or between about 39° C. and about 50° C.

Figure 8:
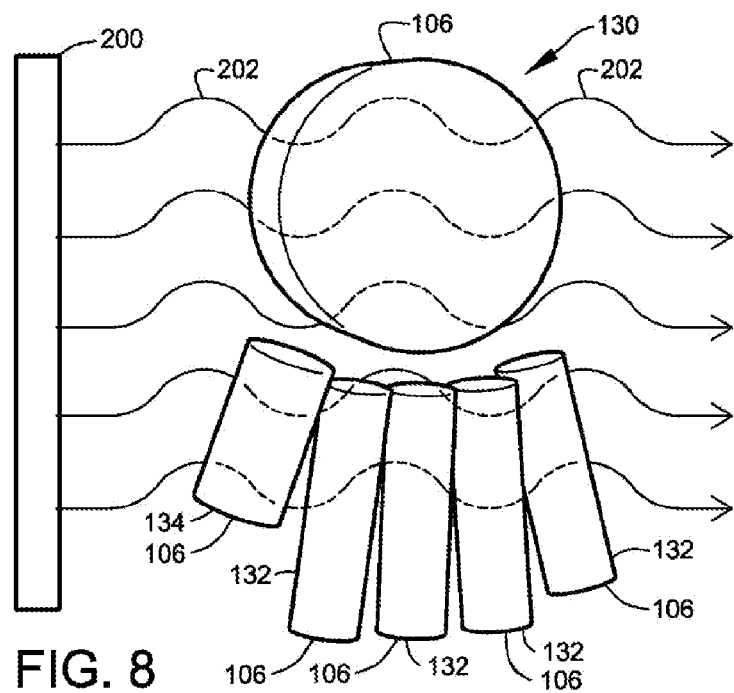
FIG. 8 shows a diagrammatic view illustrating heating of a therapeutic composition.

In a traditional commercial setting for skin therapy, the customary melt time for standard paraffin is approximately 10-15 minutes or longer in a standard non-commercial microwave (750-1000 watts) depending on the quantity being heated. Such a period of heating time is too long and thus not ideal. Further, as shown in FIG. 8, it was observed that uneven heating occurs in therapeutic composition 106 when the therapeutic composition 106 is enclosed in a body part shaped encaser 120 such as a glove or a booty, when using microwave heating. This uneven heating causes the fingers and thumb in a glove to have a substantially higher temperature than the palm area when the same therapeutic composition 106 is used in all areas. Not to be bound by theory, it is believed that due to the dielectric heating effect of microwaves 202 from microwave producer 200, variations in volumes and surface areas of therapeutic composition 106 in various areas of single-use glove 102 cause variations in microwave absorption. In order to compensate for the variation in microwave absorption, and thus the particular amount of heat absorbed, between finger composition 132, thumb composition 134, and palm composition 130, the formulations of the therapeutic composition 106 were further modified such that the uniform melting of the therapeutic composition 106 in a body part shaped encaser 120 is achieved.

To reduce the melting time of a paraffin based therapeutic composition 106, various nut or seed oils including safflower oil, vitamin E oil, coconut oil, among other oils, were tested for their effects of paraffin wax melting time after being mixed with the paraffin wax. Theoretically, the use of oils helps to lower the initial viscosity of the paraffin composition and accelerates the melting process. However, not all tested oils can achieve that purpose. An ideal melting time for the therapeutic composition 106 of the skin therapy system 100 disclosed here in is between about 1 to 2 minutes depending on the heating sources.

During testing, many different types of oils, once mixed with the paraffin wax, made the melted paraffin wax runny and would not allow the wax to re-form or re-solidify. Some seed or nut oils don't even mix well with paraffin. In addition, re-solidification or gelification may occur for easy application and removal of the skin therapy system 100 during and after the therapy. Surprisingly, the mixing of coconut oil with the paraffin is homogenized and, at certain range of ratio, the mixture allowed re-solidification or gelification of the paraffin-based therapeutic composition 106, when achieving a comparatively shortened melt time. This property for a therapeutic composition 106 may be achieved due to coconut oil forming a more solid state in comparison to other oils at typical room temperatures (below about 80 degrees Fahrenheit). Shortened time of melting and re-solidification or gelification is desirable, in that it shortens the preparation time and enables the formation and shaping of the therapeutic composition 106 into a body part shape much easier and faster either during the therapy or before and after the therapeutic composition 106 is enclosed in a body part shaped encaser 120 of the skin therapy system 100 as disclosed herein. In one embodiment, a paraffin based therapeutic composition 106 of the skin therapy system 100 as disclosed herein comprises paraffin and one or more nut oils including coconut oil. In one embodiment, a paraffin based therapeutic composition 106 of the skin therapy system 100 may comprise paraffin and coconut oil.

Continued experimentation with formulations by adding and changing combinations of paraffin and coconut oil revealed, surprisingly, that the best combination for the therapeutic composition to hold up on the skin with a body part shaped, shell-like effect while still melting in under 2 minutes is to mix the paraffin with coconut oil at a ratio of from about 1:3 to about 3:1, by weight of the therapeutic composition 106. Some variations are utilized in such a mixture as described herein to assist even-melting in a given glove or boot or other body part shaped encaser 120 with or without an encaser liner 116 as disclosed herein.

In one embodiment, the therapeutic composition 106 of the skin therapy system 100 may comprise paraffin and at least one of a seed oil and a nut oil. In some embodiments, the concentration of paraffin may be in a range of about 25 wt % to about 75 wt %. In some embodiments, the at least one of the seed oil and nut oil in the therapeutic composition 106 may comprise coconut oil. In various embodiments, the coconut oil may be at a concentration in a range of about 25 wt % to about 75 wt %. In some embodiments, the therapeutic composition 106 of the skin therapy system 100 comprises from about 30 wt % to about 60 wt % of coconut oil and from about 40 wt % to about 70 wt % of paraffin. In one embodiment, the therapeutic composition 106 of the skin therapy system 100 comprises from about 35 wt % to about 55 wt % of coconut oil and from about 45 wt % to about 65 wt % of paraffin. In one embodiment, the therapeutic composition 106 of the skin therapy system 100 comprises about 50 wt % of coconut oil and about 50 wt % of paraffin.

To achieve a simultaneously complete melting of all compositions in a body part shaped encaser 120, other alterations to change the latent heat of fusion of composition in fingers, toes, palm and anchor of the encaser 120 were tested, for example by using two or more different therapeutic compositions 106 at different portions of a body part shaped encaser 120. Without being bound by theory, more heat absorption is required in areas previously overheated and less heat absorption is required in areas previously under-heated to effect a change in the state of matter from solid to liquid. As such, having various latent heats, each therapeutic composition 106 may melt and achieve a temperature within the ideal temperature range after the same amount of time exposed to a heating source such as microwave. In one embodiment, the palm composition 130 for a hand shaped encaser comprises at least about 25 wt % to about 75 wt % of paraffin and 25 wt % to about 75 wt % of coconut oil; and the finger composition 132 and thumb composition 134 for a hand shaped encaser comprise at least 50 wt % to 70 wt % of paraffin and at least about 30 wt % to about 50 wt % of coconut oil.

Various embodiments of the therapeutic composition 106 may comprise various cannabinoid-containing extracts of Cannabis (*Cannabis indica* and/or *Cannabis sativia*) plants for transdermal delivery of the cannabinoids. In some embodiments the cannabinoid may comprise the non-psychotropic alkaloid cannabidiol (also referred to as CBD). In other embodiments, the cannabinoid may comprise the non-psychotropic cannabidiolic acid (CBDA). CBDA may be converted to CBD through heating which causes decarboxylation of CBDA.

Accordingly, the therapeutic composition 106 may comprise a broad-spectrum CBD, a full-spectrum CBD, an isolate of a CBD, a CBDA, or any combination thereof. In some embodiments, the therapeutic composition 106 comprises a broad-spectrum CBD oil. The broad-spectrum CBD may contain tetrahydrocannabinol (THC). Since the melting point is above 70° C., the THC remains in the paraffin wax when the therapeutic composition 106 is heated between 35° C. (113° F.) to about 55° C. (131° F.). An advantage of using an isolate CBD is targeting a condition with a specific cannabinoid, without any THC in the isolate CBD.

Transdermal delivery of CBD through the CBD-containing therapeutic composition 106 may provide the benefits of topically administered CBD such as alleviating wound-related pain, accelerating wound healing, reducing the need for opioid analgesics for controlling pain in skin conditions. CBD-containing therapeutic composition 106 may also improve conditions of deeper tissues such as peripheral neuropathic pain, fibromyalgia, osteoarthritis, and musculoskeletal pain. CBD may also provide anti-aging and anti-oxidant benefits to the skin. CBD may also have anti-inflammatory properties that may improve skin conditions such as acne, psoriasis, and/or eczema. The anti-inflammatory properties of CBD may compliment the anti-inflammatory properties of paraffin itself in the therapeutic composition 106. The benefits of topical CBD are further evidenced by its lack of systemic side effects, its ease of be self-administration by the consumer, and its rapid onset of analgesia.

The addition of CBD to the therapeutic composition 106 may retain the desired melting temperature of the therapeutic composition 106 of approximately about 45° C. (113° F.) to about 55° C. (131° F.), as discussed below. In various embodiments, the CBD may be stable within a homogenous mixture of the therapeutic composition 106 such that the CBD binds well with seed and/or nut oils, such as coconut oil. For example, the therapeutic composition 106 comprising coconut oil, paraffin, and CBD may be mixed and may maintain efficient dispersion, avoiding phase separation.

In some embodiments, the therapeutic composition 106 can be produced by mixing of coconut oil with the paraffin at a temperature greater than 50° C. but less than 80° C. until it homogenized. The CBD oil contains CBD in a concentration of 20 mg/ml to 100 mg/ml. The CBD oil is heated to a temperature of greater than 65° C., which is the melting point of CBD. The heated CBD oil is then added to the homogenized mixture of coconut oil and paraffin, which is heated to a temperature of greater than 65° C. At this temperature, the mixture is homogenized, and the CBD oil can be blended into the coconut oil. Optional additives including, but not limited to, fragrances, colors, emollients, essential oils, oil soluble vitamins and/or anti-oxidants, known in the art, can be added to the homogenized mixture of CBD, coconut oil, and paraffin to create the therapeutic composition 106. The volume between the encaser 120 and the encase liner 116 is filled with the therapeutic composition 106 at a temperature above 60° C.

The CBD-containing therapeutic composition 106 may comprise a therapeutically effective amount of CBD. In some embodiments, the CBD may comprise a commercially available CBD oil and/or CBD wax. In an exemplary embodiment, the CBD-containing therapeutic composition 106 may comprise at least approximately 2 milligrams of CBD per kilogram of CBD-containing therapeutic composition 106. In another exemplary embodiment, the amount of CBD in the CBD-containing therapeutic composition 106 may be approximately 2 to approximately 100 milligrams per kilogram. In another exemplary embodiment, the amount of CBD in the CBD-containing therapeutic composition 106 may be approximately 50 milligrams within each skin therapy system 100.

In some embodiments, the therapeutic composition 106 comprises paraffin, coconut oil, and CBD. For example, the therapeutic composition 106 can comprise paraffin, and coconut oil in a ratio in a range from 4:1 to 2:1 and CBD in a range of 5 mg/kg of a combination of paraffin and coconut oil to 100 mg/kg of a combination of paraffin and coconut oil. In some examples, the amount of CBD in a single encaser 120 is 5 mg and total of 10 mg for a pair of encasers 120.

In some embodiments, a paraffin based therapeutic composition 106 of the skin therapy system 100 can comprise paraffin, coconut oil and CBD.

In some examples, the amount of CBD in a single encaser 120 is 25 mg and total of 50 mg for a pair of encasers 120. In some examples, the amount of CBD in a single encaser 120 is 50 mg and total of 100 mg for a pair of encasers 120. In one example, the amount of CBD in a single encaser 120 is 100 mg and total of 200 mg for a pair of encasers 120.

Without being bound by theory, the CBD is transported in the coconut oil through the encase liner 116 and into the skin when the temperature of the therapeutic composition 106 is between 48° C. (119° F.) to about 51° C. (124° F.). The heat is the transportation mechanism for moving the CBD from the therapeutic composition 106 to the skin surface of the user.

Various embodiments of the CBD-containing therapeutic composition 106 may further comprise various additives such as steroids. For example, the steroid may be 1% hydrocortisone.

Therapeutic composition 106 as disclosed herein may further comprise at least one essential oil. For medical purposes, from about six to about twelve drops of medical grade essential oils may be added to the therapeutic composition 106. A drop of essential oils, as defined herein using the AFNOR-ISO standard for quantifying essential oils, is about $\frac{1}{20}^{th}$ of one milliliter when utilizing the standard of 20 drops per milliliter of essential oil. When the standard for a specific essential oil is different due to viscosity, a single-drop volume may be adjusted accordingly. In one embodiment, the essential oils are added and mixed into the therapeutic composition 106 before the therapeutic composition 106 is enclosed in a body part shaped encaser 120 of the skin therapy system 100. In one embodiment, the essential oils are added into the therapeutic composition 106 prepackaged in a body part shaped encaser 120 of the skin therapy system 100 upon applying the same to a targeted skin area, such that different essential oils may be used for a specific condition of a specific individual under the therapy. Essential oils and aromatic oils of the therapeutic composition 106 may be selected from peppermint oil, cinnamon leaf oil, lemongrass oil, clove oil, castor oil, orange oil, eucalyptus oil, tea tree oil, wintergreen oil, patchouli oil, lavender, bergamot, sandalwood, chamomile, aldehyde C16, α-terpineol, amyl cinnamic aldehyde, amyl salicylate, anisic aldehyde, benzyl alcohol, benzyl acetate, cinnamaldehyde, cinnamic alcohol, carvacrol, carveol, citral, citronellal, citronellol, p-cymene, diethyl phthalate, dimethyl salicylate, dipropylene glycol, eucalyptol, eugenol, iso-eugenol, galaxolide, geraniol, guaiacol, ionone, menthol, methyl salicylate, methyl anthranilate, methyl ionone, α-phellandrene, pennyroyal oil, perillaldehyde, 1- or 2-phenyl ethyl alcohol, 1- or 2-phenyl ethyl propionate, piperonal, piperonyl acetate, piperonyl alcohol, D-pulegone, terpinen-4-ol, terpinyl acetate, 4-tert butylcyclohexyl acetate, thyme oil, thymol, metabolites of trans-anethole, vanillin, ethyl vanillin, and combinations thereof.

In one embodiment, an essential oil mixture for pain relieving comprises peppermint oil, cinnamon leaf oil, clary sage, and orange oil. In one embodiment, an essential oil mixture for anti-fungal and anti-bacterial effects comprises tea tree oil, clove oil, lemon oil, eucalyptus oil and patchouli oil. In one embodiment, an essential oil mixture for relaxation comprises lavender, bergamot, sandalwood and chamomile. Additionally, aromatherapy oils may also be utilized to add further therapeutic effects. In one embodiment, the therapeutic composition 106, comprising paraffin and coconut oil, may further comprise at least one aromatic oil.

The paraffin based therapeutic composition 106 may further comprise optional additives including, but not limited to fragrances, colors, emollients, and antioxidants, known in the art. The antioxidant may be natural or synthetic. Suitable antioxidants include, but are not limited to, ascorbic acid and its salts, ascorbyl palmitate, ascorbyl stearate, anoxomer, N-acetylcysteine, benzyl isothiocyanate, m-aminobenzoic acid, o-aminobenzoic acid, p-aminobenzoic acid (PABA), butylated hydroxyanisole (BHA), butylated hydroxytoluene (BHT), caffeic acid, canthaxantin, alpha-carotene, beta-carotene, beta-carotene, beta-apo-carotenoic acid, carnosol, carvacrol, catechins, cetyl gallate, chlorogenic acid, citric acid and its salts, clove extract, coffee bean extract, p-coumaric acid, 3,4-dihydroxybenzoic acid, N,N'-diphenyl-p-phenylenediamine (DPPD), dilauryl thiodipropionate, distearyl thiodipropionate, 2,6-di-tert-butylphenol, dodecyl gallate, edetic acid, ellagic acid, erythorbic acid, sodium erythorbate, esculetin, esculin, 6-ethoxy-1,2-dihydro-2,2,4-trimethylquinoline, ethyl gallate, ethyl maltol, ethylenediaminetetraacetic acid (EDTA), eucalyptus extract, eugenol, ferulic acid, flavonoids (e.g., catechin, epicatechin, epicatechin gallate, epigallocatechin (EGC), epigallocatechin gallate (EGCG), polyphenol epigallocatechin-3-gallate), flavones (e.g., apigenin, chrysin, luteolin), flavonols (e.g., datiscetin, myricetin, daemfero), flavanones, fraxetin, fumaric acid, gallic acid, gentian extract, gluconic acid, glycine, gum guaiacum, hesperetin, alpha-hydroxybenzyl phosphinic acid, hydroxycinammic acid, hydroxyglutaric acid, hydroquinone, N-hydroxysuccinic acid, hydroxytyrosol, hydroxyurea, rice bran extract, lactic acid and its salts, lecithin, lecithin citrate; R-alpha-lipoic acid, lutein, lycopene, malic acid, maltol, 5-methoxy tryptamine, methyl gallate, monoglyceride citrate; monoisopropyl citrate; morin, beta-naphthoflavone, nordihydroguaiaretic acid (NDGA), octyl gallate, oxalic acid, palmityl citrate, phenothiazine, phosphatidylcholine, phosphoric acid, phosphates, phytic acid, phytylubichromel, pimento extract, propyl gallate, polyphosphates, quercetin, trans-resveratrol, rosemary extract, rosmarinic acid, sage extract, sesamol, silymarin, sinapic acid, succinic acid, stearyl citrate, syringic acid, tartaric acid, thymol, tocopherols (i.e., alpha-, beta-, gamma- and delta-tocopherol), tocotrienols (i.e., alpha-, beta-, gamma- and delta-tocotrienols), tyrosol, vanilic acid, 2,6-di-tert-butyl-4-hydroxymethylphenol (i.e., Ionox 100), 2,4-(tris-3',5'-bi-tert-butyl-4'-hydroxybenzyl)-mesitylene (i.e., Ionox 330), 2,4,5-trihydroxybutyrophenone, ubiquinone, tertiary butyl hydroquinone (TBHQ), thiodipropionic acid, trihydroxy butyrophenone, tryptamine, tyramine, uric acid, vitamin K and derivatives, vitamin Q10, wheat germ oil, zeaxanthin, or combinations thereof. One skilled in the art will appreciate that the antioxidants incorporated into the composition (including those listed herein) encompass all potential salt and ester forms of the antioxidants in addition to the pure forms of the compound. In some embodiments, the antioxidant may comprise a vitamin E compound such as tocopheryl acetate, tocopheryl linoleate, tocopheryl tocopherol nicotinate, tocopheryl succinate, ascorbyl tocopheryl phosphate, dioleyl tocopheryl methylsilanol, tocophersolan, and tocopheryl linoleate/oleate. In one embodiment, included in the vitamin E oil are traces of safflower oil, and other oils. In another embodiment, the vitamin E formula further comprises the largest amount of sunflower seed oil followed by safflower seed oil, tocopheryl acetate, rice bran oil, almond oil, apricot oil, wheat germ oil and lecithin. In one embodiment of the therapeutic composition 106 comprising paraffin at a concentration in a range of about 25 wt % to about 75 wt % and coconut oil at a concentration in a range of about 25 wt % to about 75 wt %, the therapeutic composition 106 further comprises from about 2 wt % to 7 wt % of a mixture of antioxidant.

The therapeutic composition 106 of the skin therapy system 100 may be a liquid-based composition, such that a solid to liquid, then back to solid phase changes are not involved. In some embodiments, a pre-heating or pre-cooling step before application may be required. In some other embodiments, a pre-heating or pre-cooling step before application may not be required. In one embodiment, the liquid-based composition comprises a therapeutic composition 106 comprising alpha hydroxy acid including lactic acid and glycolic acid; and/or beta hydroxy acid including salicylic acid, and any combination thereof. The liquid based composition comprising alpha hydroxy acid including lactic acid and glycolic acid; and/or beta hydroxy acid including salicylic acid may further comprise essential oils, fragrances, colors, emollients, anti-oxidants, and other additives including absorbent, adsorbent, pH controller, and substances for rehydration known in the art. In one embodiment, a liquid based therapeutic composition 106 for the skin therapy system 100 comprises lactic acid, glycolic acid, salicylic acid, lemon oil, polyquaternium-10, PEG-40 hydrogenated castor oil, sodium hydroxide, and one or more antioxidant including vitamin E. Various suitable essential oils and anti-oxidants for a liquid-based therapeutic composition 106 are described above in detail.

This technology also provides a method relating to providing skin treatment utilizing a therapeutic composition 106 contained in a body part shaped encaser 120 amenable to various heating elements to provide liquefaction before use without burning the skin. The method of using the skin therapy system 100 as disclosed herein for skin treatment generally comprises the steps of heating the encaser 120 containing a therapeutic composition 106 using one or more heating elements, applying the unsealed encaser 120 to targeted skin area by attaching the encaser 120 to a body part, and removing the encaser 120 from the targeted skin area at the end of the therapy.

Some paraffin based therapeutic compositions 106 need to be heated to melt prior to application. Paraffin wax typically has a melting point temperature in the range between about 46° C. (114.8° F.) and about 68° C. (154.4° F.). Petroleum jelly based therapeutic compositions 106 have a melting-point usually within a few degrees of human body temperature, which is approximately 37° C. (98.6° F.). Liquid paraffin-based therapeutic composition 106 and other liquid based composition may need to be pre-heated to body temperature for the comfortable feel to the skin upon application. Depending on the storage condition, room temperature, and specific therapeutic temperature requirement, the therapeutic composition 106 enclosed in a body part shaped encaser 120 of the skin therapy system 100 as disclosed herein may require a heating process by a heating element. Suitable heat element may be selected from microwave oven, stove, hot towel cabinet, heating coils, heating pad, heater, heating lamp, warmer, radiator, boiler, steamer (such as a towel steamer), warm water bath, hydrocollator, and any other device or equipment known in the art. In one embodiment, the heating element may be portable.

In some embodiments, the heating element is comprised in the skin therapy system 100. The heating temperature may be provided by a heating element included in the skin therapy system 100, and the temperature of the therapeutic composition 106 may be indicated by touching or temperature indicator attached to the body part shaped encaser 120 of the skin therapy system 100. With a heating time of a therapeutic composition 106 between 1-5 minutes, or preferably 1-2 minutes, for even melting of the composition, a melting temperature of the therapeutic composition 106 ranges from about 45° C. (113° F.) to about 55° C. (131° F.). With a heating time of a therapeutic composition 106 between 1-2 minutes for even melting of the composition, a melting temperature of the therapeutic composition 106 ranges from about 48° C. (119° F.) to about 51° C. (124° F.). In one embodiment, the therapeutic composition 106 may comprise paraffin at a concentration of about 25-75 wt %, by weight of the composition, and coconut oil at a concentration of about 25-75 wt % by weight of the composition and have a melting temperature between about 48° C. to about 51° C., with an even melting of the composition taking place in about 1-5 minutes.

After a predetermined temperature range of a therapeutic composition 106 of the skin therapy system 100 is reached, the sealed encaser 120 containing the therapeutic composition 106 is opened by cutting, unzipping or tearing the closure 1425 of the encaser 120. The body part is inserted into the encaser 120 such that the targeted skin area is in direct contact with the therapeutic composition 106, through touching, dipping, or being covered by the therapeutic composition 106. The encaser 120 is then attached to the body part using adhesive tape, strap, string, elastic band, or tubing for stabilization during the therapy. The application may last for 10 minutes, 20 minutes, 30 minutes, 60 minutes, 120 minutes or longer, or any range of duration in between. When the therapy ends at a time point, the encaser 120 is released from the body part by removing the body part from the encaser 120 comprising the therapeutic composition 106.

Figure 10:
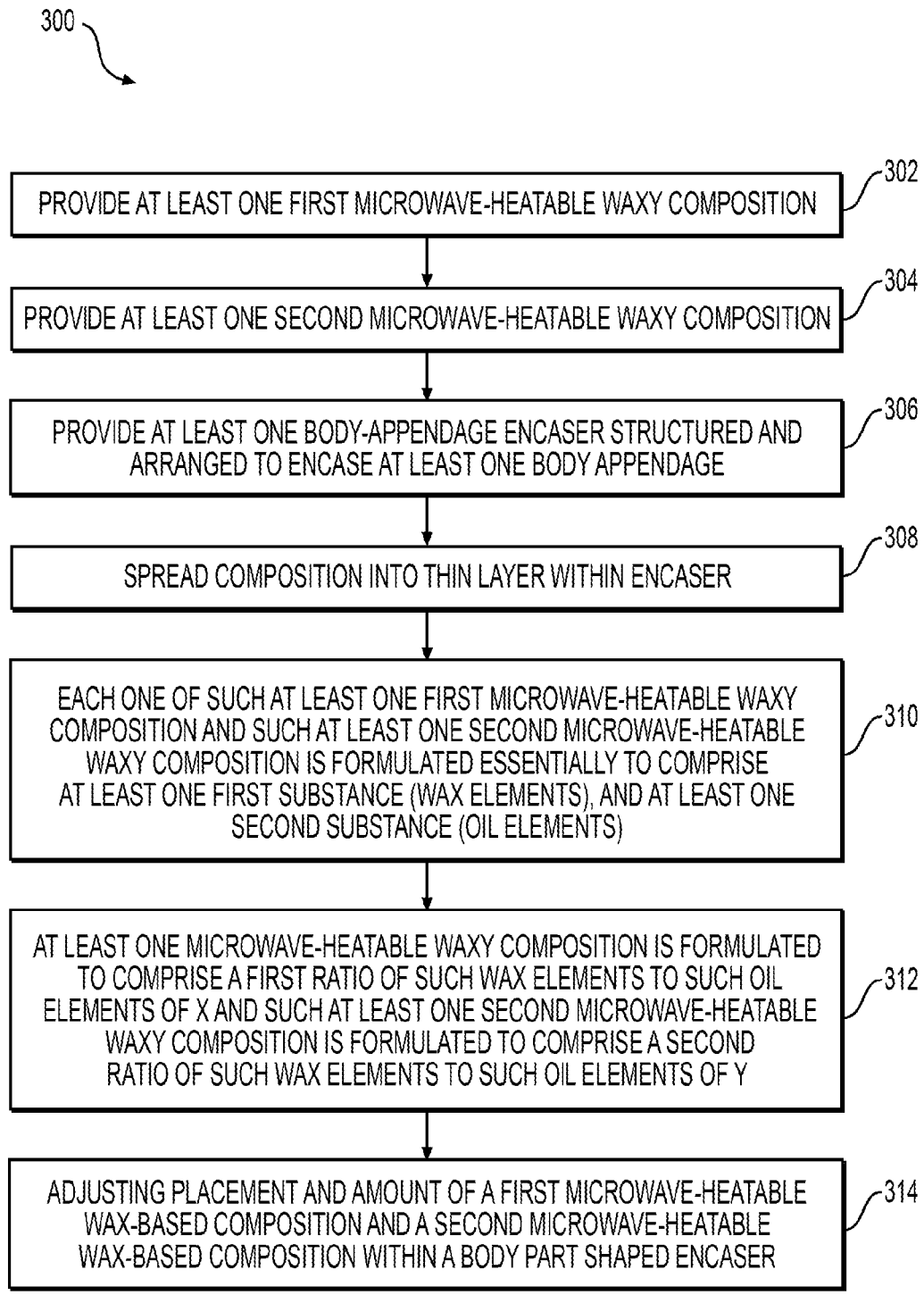
FIG. 10 is a flow chart illustrating a method of heating the therapy system.

The method of using the skin therapy system 100 as disclosed herein for skin treatment may further comprise assembling the body part shaped encaser 120. Referring to the flow diagram of FIG. 10 as an example in which a microwave oven is used as a heating element in method 300, the following steps may be followed. In initial step 302 of method 300 a first wax-based composition is formulated to be heatable by a microwave energy producer. Next, as indicated in step 304 a second microwave-heatable wax-based composition is formulated to be heatable by a microwave energy producer. Next, as indicated in step 306 at least one body part shaped encaser structured and arranged to encase a body part of a human body is provided. As indicated in Step 308 one or more microwave-heatable wax-based composition is encased by spreading the composition into a thin layer in the encaser. As indicated in Step 310 each one of such microwave-heatable wax-based composition is formulated to comprise at least one first substance, and at least one second substance; wherein such first substance comprises wax elements; wherein the second substance comprises oil elements. Step 312 indicates that a first microwave-heatable wax-based composition is formulated to comprise a first ratio X of wax elements to the oil elements, and a second microwave-heatable wax-based composition is formulated to comprise a second ratio Y of wax elements to the oil elements. The latent heat of fusion of the resulting first microwave-heatable wax-based composition may be substantially different from the latent heat of fusion of the second microwave-heatable waxy composition. Finally, as indicated in Step 314, a skin treatment utilizing such wax-based compositions amenable to microwave heating to provide liquefaction before use without skin burning may be provided by adjusting placement and amount of a first microwave-heatable wax-based composition and a second microwave-heatable wax-based composition within a body part shaped encaser to equalize the melting of the wax-based composition to assist prevention of injuring skin tissues of the body part to be treated.

Figure 6B:
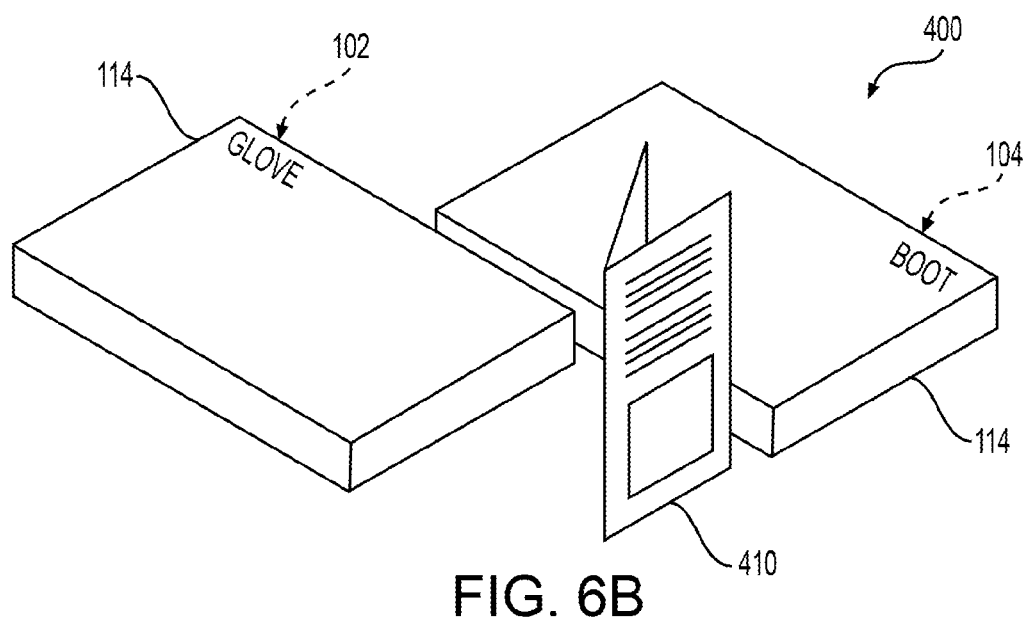
FIG. 6B shows a perspective view of the therapy system as a pre-packaged kit.

As an additional example, FIG. 6B shows an illustrative set of instructions for using a pre-packaged kit/apparatus according to an embodiment of the present technology. In one embodiment of a method of use, single-use wax-based encaser 120 may be provided as a prepackaged kit 400 (See FIG. 4A, FIG. 4B and FIG. 6A and FIG. 6B) comprising a microwavable sealing box 114 comprising at least one single-use glove 102 or single-use boot 104 comprising one or more therapeutic composition 106 and at least one set of instructions 410.

In an exemplary method of manufacture, the temperature indicator 118, such as temperature activated ink, may be sprayed, printed, stamped, and/or otherwise applied to at least one of the first and second substrates of film 1410, 1415 that form the encaser 120. The encaser liner 116 may be layered between the first and second substrates of film 1410, 1415. A hot compress having an outline of a desired body part shape may be applied to the layered stack of the first and second substrates of film 1410, 1415 and the encaser liner 116. The hot compress may melt the layered stack forming the first hermetic seal 1400 and affixing the encaser liner's 116 position within the internal volume of the encaser 120 while also creating a first fillable space between the first substrate of film 1410 and a first layer of the encaser liner 116 (top space layer) and a second fillable space between the second substrate of film 1415 and a second layer of the encaser liner 116 (bottom space layer).

The therapeutic composition 106 may be poured or otherwise placed into the two fillable spaces (top and bottom spaces). Once complete, a second hermetic seal (corresponding to the at least one hermetic seal 1402 of FIG. 14) may be formed between the first substrate of film 1410 and the first layer of the encaser liner 116 to seal the therapeutic composition 106 in place within the first fillable space (top space). Similarly, a third hermetic seal (corresponding to the at least one hermetic seal 1402 of FIG. 14) may be formed between the second substrate of film 1415 and the second layer of the encaser liner 116 to seal the therapeutic composition 106 within the second fillable space (bottom space). Finally, a closure element 1425 may be included between the hand aperture 140 and the second and third hermetic seals to seal off the entire internal volume of the encaser 120 and the internal volume of the encaser liner 116 from the surrounding environment.

Figure 15:
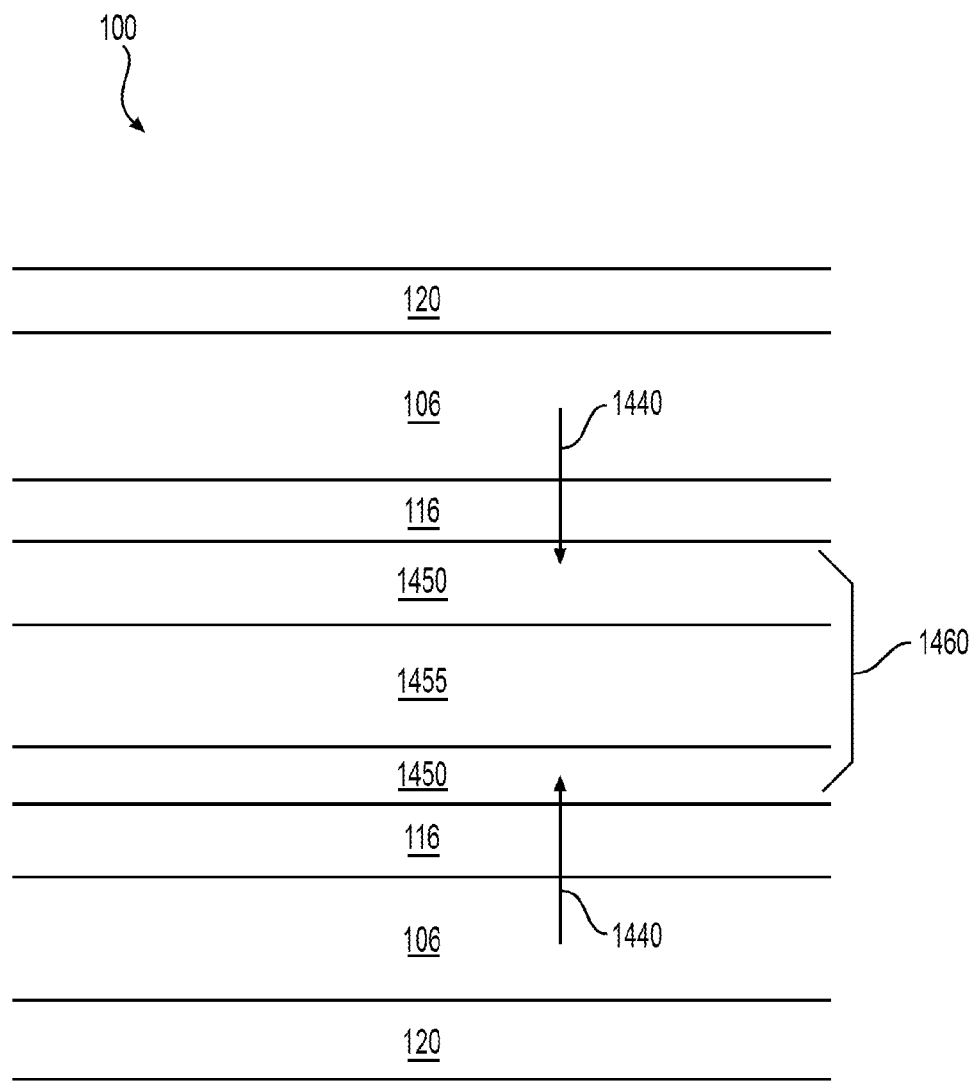
FIG. 15 is an exemplary cross-section view of a skin therapy system, which illustrates various methods of skin therapy.

With reference to FIG. 15, an exemplary cross-section view of a skin therapy system 100 illustrates various methods of skin therapy. Various embodiments provide a skin therapy system 100 comprising an encaser 120, an encaser liner 116, and a therapeutic composition 106 positioned in a fillable space between the encaser 120 and the encaser liner 116. The encaser 120 has a top portion formed by a first film substrate and a bottom portion formed by a second film substrate. The fillable space is a volume defined by the inner surface of the encaser 120 and the outer surface of the encaser liner 116, which are connected at the cuff of the encaser 120. In some embodiments, the fillable space is a volume defined by the inner surface of the encaser 120 and the outer surface of the encaser liner 116, which are connected at the cuff of the encaser 120 and connected at the fingertips (and thumb tip) of the encaser 120. In these embodiments, a fillable space is located on both of the outer surfaces of the encaser liner 116 and the encaser liner 116 is held in place by the connections to the encaser 120 at the fingertips when user pulls a body part (such as, for example a hand) out of the skin therapy system 100. The skin therapy system 100 has a thermochromatic indicator disposed on the first film substrate to be viewable on the top portion and a second thermochromatic indicator disposed on the first film substrate at a second location different from that of the thermochromatic indicator disposed on the first film substrate.

The therapeutic composition 106 is held in the fillable space by the encaser liner 116 and the therapeutic composition 106 is not in contact with a user's skin 1450. The encaser liner 116 can made of non-woven polypropylene fabric (or an equivalent material), which is permeable to one or more ingredients of the therapeutic composition 106 at an elevated temperature in a range from 45° C. (113° F.) to 55° C. (131° F.).

For example, a therapeutic composition 106 comprises paraffin and coconut oil, as described herein. If the therapeutic composition 106 is at the elevated temperature in a range from 45° C. (113° F.) to 55° C. (131° F.), a portion of the coconut oil is thermally transported 1440 through the encaser liner 116 and onto the skin 1450 of a body part 1460. In another example, a therapeutic composition 106 comprises paraffin, coconut oil, and vitamin E, as described herein. If the therapeutic composition 106 is at the elevated temperature in a range from 45° C. (113° F.) to 55° C. (131° F.), a portion of the coconut oil and the vitamin E is thermally transported 1440 through the encaser liner 116 and onto the skin 1450 of a body part 1460. Other examples include a therapeutic composition 106 comprising paraffin, coconut oil, and an essential oil, as descried herein. If the therapeutic composition 106 is at the elevated temperature in a range from 45° C. (113° F.) to 55° C. (131° F.), a portion of the coconut oil and the essential oil is thermally transported 1440 through the encaser liner 116 and onto the skin 1450 of a body part 1460. In these examples, the paraffin is blocked by the encaser liner 116 and the paraffin does not make contact with the skin 1450.

As illustrated in FIG. 15, the body part 1460 is defined by the skin 1450 on either side of the internal structure 1455 of the body part 1460. For example, the body part can be a finger, a thumb, a hand, a toe, a foot, a part of a leg, or a part of an arm.

Various embodiments provide methods of treating the skin. For example, a method can include providing a skin therapy system 100 comprising an encaser 120, an encaser liner 116, and a therapeutic composition 106 positioned in a fillable space between the encaser 120 and the encaser liner 116 and heating the therapeutic composition 106 at an elevated temperature in a range from 35° C. to 55° C. The method can include inserting a body part 1460 into an opening of the encaser 120 and contacting skin surface 1450 surrounding the body part 1460 with the encaser liner 116. The method can include keeping the skin surface 1450 in contact with the encaser liner 116 while the therapeutic composition 106 is at the elevated temperature and thermally transporting 1440 at least one ingredient from the therapeutic composition on to the skin 1450. The method can include blocking the paraffin from reaching the skin 1450. The at least one ingredient can be coconut oil. The at least one ingredient can be vitamin E. The at least one ingredient can be lanolin. The treating the skin can be adding moisture to dry skin 1450. The treating the skin can reduce cracks in the skin 1450. The treating the skin can be relieving pain from arthritis. The treating the skin can be a skin therapy.

Figure 16:
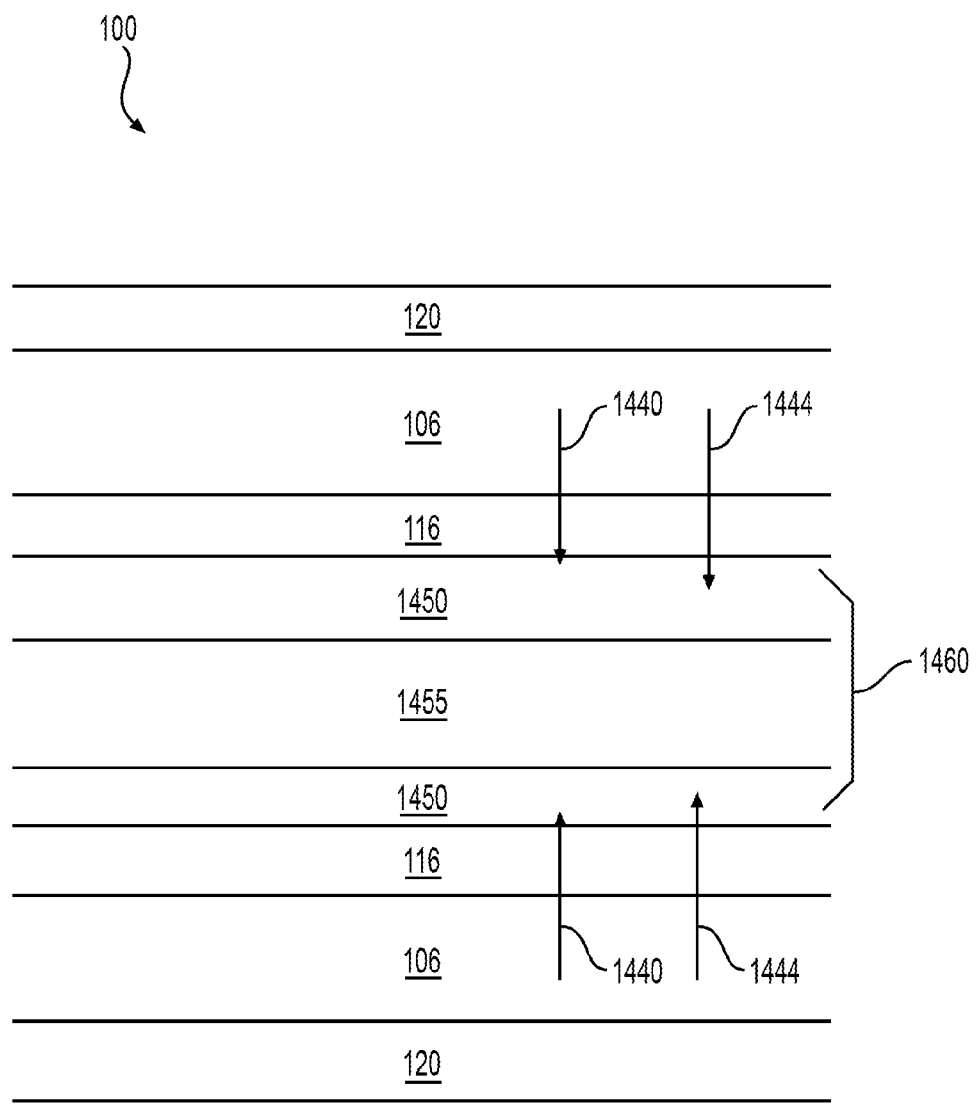
FIG. 16 is an exemplary cross-section view of a skin therapy system, which illustrates various methods of transdermal delivery of a medicinal.

Finally moving to FIG. 16, an exemplary cross-section view of the skin therapy system 100 illustrates various methods of transdermal delivery of a medicinal. Some embodiments employ various materials for containing heat-stable therapeutic compositions 106 which may be practiced in conjunction with any number of compositions and procedures for treating pain and inflammation of joints and other body parts and the systems described are merely exemplary applications for the technology. Various representative implementations of these embodiments may be applied to any portion of the human body for the treatment of skin, pain, injury, and/or inflammatory medical conditions.

In some embodiments, the treating the skin can be reducing inflammation in the internal structure 1455 of the body part 1460. Examples of the internal structure 1455 can be a muscle, a tendon, a ligament, or connecting tissue. In some embodiments, the thermally transporting 1440 at least one ingredient from the therapeutic composition on to the skin 1450 can include transporting 1444 the at least one ingredient through the skin 1450 and into the internal structure 1455 of the body part 1460. Some embodiments can include treating a sprain in the internal structure 1455 of a body part 1460, which can include thermally transporting 1444 at least one ingredient from the therapeutic composition into the internal structure 1455 of the body part 1460. In some examples of these embodiments, the therapeutic composition 106 can include an medically active ingredient and the medically active ingredient can be thermally transported 1444 into the internal structure 1455 of the body part 1460 and treating at least one of a muscle, a tendon, a ligament, or connecting tissue. A medically active ingredient can be at least one of an anti-inflammatory, an antioxidant, a steroid, an essential oil, and combinations thereof.

For example, a therapeutic composition 106 comprises paraffin, coconut oil, and a medically active ingredient, as described herein. If the therapeutic composition 106 is at the elevated temperature in a range from 45° C. (113° F.) to 55° C. (131° F.), a portion of the coconut oil is thermally transported 1440 through the encaser liner 116 and onto the skin 1450 of a body part 1460 and the medically active ingredient is thermally transported 1444 into the skin 1450 and can be thermally transported 1444 into the internal structure 1455 of the body part 1460. In another example, a therapeutic composition 106 comprises paraffin, coconut oil, vitamin E, and a medically active ingredient, as described herein. If the therapeutic composition 106 is at the elevated temperature in a range from 45° C. (113° F.) to 55° C. (131° F.), a portion of the coconut oil and the vitamin E is thermally transported 1440 through the encaser liner 116 and onto the skin 1450 of a body part 1460 and the medically active ingredient is thermally transported 1444 into the skin 1450 and can be thermally transported 1444 into the internal structure 1455 of the body part 1460. Other examples include a therapeutic composition 106 comprising paraffin, coconut oil, an essential oil, and a medically active ingredient, as descried herein. If the therapeutic composition 106 is at the elevated temperature in a range from 45° C. (113° F.) to 55° C. (131° F.), a portion of the coconut oil and the essential oil is thermally transported 1440 through the encaser liner 116 and onto the skin 1450 of a body part 1460 and the medically active ingredient is thermally transported 1444 into the skin 1450 and can be thermally transported 1444 into the internal structure 1455 of the body part 1460. In these examples, the paraffin is blocked by the encaser liner 116 and the paraffin does not make contact with the skin 1450.

In some embodiments, the medically active ingredient is CBD. Without being bound by theory, the CBD is transported in the coconut oil through the encaser liner 116 and into the skin when the temperature of the therapeutic composition 106 is between 48° C. (119° F.) to about 51° C. (124° F.). The heat is the transportation mechanism for moving the CBD from the therapeutic composition 106 to the skin surface of the user. The heat provided to the skin 1450 by the heated therapeutic composition 106 increases the permeability of the skin 1450, which allows the CBD to penetrate deeper into the skin 1450 (and in some cases into the internal structure 1455) and last longer in the tissue. This enables a larger amount of CBD to reach a treatment as compared to rubbing a CBD oil with the same concentration on to one's skin at room temperature.

Method of treating inflammation comprises providing an encaser 120 having a therapeutic composition 106 comprising paraffin, coconut oil, and CBD, the therapeutic composition 106 positioned between the encaser 120 and an encaser liner 116. The method can comprise heating the therapeutic composition 106 to a temperature in the range between 48° C. (119° F.) to about 51° C. (124° F.) then contacting the encaser liner 116 to a surface of skin. The method can comprise applying heat to the surface of the skin to increase permeability of the skin and transporting an oil comprising CBD from the therapeutic composition 106 into the skin. The amount of CBD in the therapeutic composition 106 can be from 5 mg to 100 mg. The oil can also comprise coconut oil. The ratio of coconut oil to CBD in the therapeutic composition 106 is in a range from 40:1 to 5:1 by weight.

In some embodiments, a method of relieving inflammation and/or pain includes providing a skin therapy system 100 comprising an encaser 120, an encaser liner 116, and a therapeutic composition 106 comprising an therapeutic amount of CBD positioned in a Tillable space between the encaser 120 and the encaser liner 116 and thermally transporting the therapeutic amount of CBD to a targeted inflammation site in the internal structure 1455 of the body part 1460.

In some embodiments, a method of relieving stress, anxiety, and/or post-stroke depression (PSD) includes providing a skin therapy system 100 comprising an encaser 120, an encaser liner 116, and a therapeutic composition 106 comprising an therapeutic amount of CBD positioned in a Tillable space between the encaser 120 and the encaser liner 116 and thermally transporting the therapeutic amount of CBD into at least one blood vessel in the internal structure 1455 of the body part 1460.

In some embodiments, a method of delivering antioxidants includes providing a skin therapy system 100 comprising an encaser 120, an encaser liner 116, and a therapeutic composition 106 comprising an therapeutic amount of CBD positioned in a fillable space between the encaser 120 and the encaser liner 116 and thermally transporting the therapeutic amount of CBD into the internal structure 1455 of the body part 1460.

In the foregoing description, the technology has been described with reference to specific exemplary embodiments. Various modifications and changes may be made, however, without departing from the scope of the present technology as set forth. The description is to be regarded in an illustrative manner, rather than a restrictive one and all such modifications are intended to be included within the scope of the present technology. Accordingly, the scope of the technology should be determined by the generic embodiments described and their legal equivalents rather than by merely the specific examples described above. For example, the steps recited in any method or process embodiment may be executed in any appropriate order and are not limited to the explicit order presented in the specific examples. Additionally, the components and/or elements recited in any system embodiment may be combined in a variety of permutations to produce substantially the same result as the present technology and are accordingly not limited to the specific configuration recited in the specific examples.

Benefits, other advantages and solutions to problems have been described above with regard to particular embodiments. Any benefit, advantage, solution to problems or any element that may cause any particular benefit, advantage or solution to occur or to become more pronounced, however, is not to be construed as a critical, required or essential feature or component.

The terms "comprises," "comprising," or any variation thereof, are intended to reference a non-exclusive inclusion, such that a process, method, article, composition or apparatus that comprises a list of elements does not include only those elements recited, but may also include other elements not expressly listed or inherent to such process, method, article, composition or apparatus. Other combinations and/or modifications of the above-described structures, arrangements, applications, proportions, elements, materials or components used in the practice of the present technology, in addition to those not specifically recited, may be varied or otherwise particularly adapted to specific environments, manufacturing specifications, design parameters or other operating requirements without departing from the general principles of the same.

The invention claimed is:

1. A skin therapy system for skin conditioning or treatment of a body part, comprising:
 a body part shaped encaser comprising:
  a first film substrate forming a top portion of the body part shaped encaser; and
  a second film substrate forming a bottom portion of the body part shaped encaser;
 an encaser liner disposed between the first and second film substrates, wherein an outer peripheral edge of the encaser liner is sealed between outer peripheral edges of the first and second film substrates to create a hermetic seal forming:
  a first fillable space between the first film substrate and a first layer of the encaser liner;
  a second fillable space between the second film substrate and a second layer of the encaser liner; and
  an internal volume defined by the first and second layers of the encaser liner and disposed between the first and second fillable spaces, wherein the internal volume is configured to receive the body part; and
 a therapeutic composition contained within the first and second fillable spaces, wherein the first and second layers of the encaser liner are permeable to one or more ingredients of the therapeutic composition.

2. The skin therapy system according to claim 1, further comprising:
 a second hermetic seal between the first film substrate and the first layer of the encaser liner to seal the first fillable space; and
 a third hermetic seal between the second film substrate and the second layer of the encaser liner to seal the second fillable space.

3. The skin therapy system according to claim 2, further comprising a closure element positioned between the second and third hermetic seals and an access opening, wherein the access opening is configured to allow the body part to be inserted into the internal volume of the encaser liner.

4. The skin therapy system according to claim 2, further comprising a thermochromatic indicator disposed on the first film substrate to be viewable on the top portion.

5. The skin therapy system according to claim 4, further comprising a second thermochromatic indicator disposed on the first film substrate at a second location different from that of the thermochromatic indicator disposed on the first film substrate.

6. The skin therapy system according to claim 2, wherein the encaser liner comprises the same shape as the body part shaped encaser.

7. The skin therapy system according to claim 1, wherein the encaser liner comprises polypropylene fabric.

8. The skin therapy system according to claim 1, wherein the encaser liner comprises paper sheet.

* * * * *